US012630584B2

(12) United States Patent
Roy et al.

(10) Patent No.: US 12,630,584 B2
(45) Date of Patent: May 19, 2026

(54) COMPUTATIONAL DESIGN OF ALPHA(V) BETA (6) INTEGRIN BINDING PROTEINS

(71) Applicants: UNIVERSITY OF WASHINGTON, Seattle, WA (US); CHILDREN'S MEDICAL CENTER CORPORATION, Boston, MA (US)

(72) Inventors: Anindya Roy, Seattle, WA (US); Lei Shi, Seattle, WA (US); Xianchi Dong, Boston, MA (US); Jing Li, Boston, MA (US); Timothy Springer, Boston, MA (US); David Baker, Seattle, WA (US)

(73) Assignees: UNIVERSITY OF WASHINGTON, Seattle, WA (US); CHILDREN'S MEDICAL CENTER CORPORATION, Boston, MA (US)

( * ) Notice: Subject to any disclaimer, the term of this patent is extended or adjusted under 35 U.S.C. 154(b) by 887 days.

(21) Appl. No.: 17/763,772

(22) PCT Filed: Oct. 23, 2020

(86) PCT No.: PCT/US2020/057016
§ 371 (c)(1),
(2) Date: Mar. 25, 2022

(87) PCT Pub. No.: WO2021/081301
PCT Pub. Date: Apr. 29, 2021

(65) Prior Publication Data
US 2022/0348609 A1 Nov. 3, 2022

Related U.S. Application Data

(60) Provisional application No. 62/925,868, filed on Oct. 25, 2019.

(51) Int. Cl.
*C07K 7/00* (2006.01)
*A61K 38/00* (2006.01)
*A61P 35/00* (2006.01)
*C07K 14/495* (2006.01)

(52) U.S. Cl.
CPC ............... *C07K 7/00* (2013.01); *A61P 35/00* (2018.01); *C07K 14/495* (2013.01); *A61K 38/00* (2013.01)

(58) Field of Classification Search
CPC ......... C07K 7/00; C07K 14/495; A61K 38/00
See application file for complete search history.

(56) References Cited

U.S. PATENT DOCUMENTS 9,206,237 B2 12/2015 Kimura et al.
2009/0130098 A1 5/2009 Goodman et al.
2016/0047813 A1 2/2016 Rogler et al.

FOREIGN PATENT DOCUMENTS

WO 2014/143739 9/2014
WO WO-2014143739 A2 * 9/2014 ......... C07K 16/2839
WO 2017/218569 12/2017
WO 2018/085415 5/2018

OTHER PUBLICATIONS

Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Bork. Powers and Pitfalls in Sequence Analysis: The 70% Hurdle. Genome Research, 2000; 10:398-400 (Year: 2000).*
Buss et al: "Specific high affinity interaction of CagI with integrin avb6 promotes type IV secretion of CagA into human cells", FEBS Journal, vol. 286, No. 20, Oct. 1, 2019 (Oct. 1, 2019), pp. 3980-3997.
Bonsor et al: "Integrin Engagement by the Helical RGD Motif of the Helicobacter pylori CagL Protein Is Regulated by pH-induced Displacement of a Neighboring Helix", Journal of Biological Chemistry, vol. 290, No. 20, May 15, 2015 (May 15, 2015), pp. 12929-12940.
Dong et al: "Structural determinants of integrin [beta]-subunit specificity for latent TGF-[beta]", Nat. Struct. Mol. Biol., vol. 21, No. 12, Nov. 10, 2014 (Nov. 10, 2014), pp. 1091-1096.
Slack, et al., (2016) "Discovery of a Novel, High Affinity, Small Molecule avB6 Inhibitor for the Treatment of Idiopathic Pulmonary Fibrosis," QJM vol. 109, Issue suppl_1 pp. S60.
Kimura, et al., (2012) "Pharmacokinetically Stabilized Cystine Knot Peptides that Bind Alpha-v-Beta-6 Integrin with Single-Digit Nanomolar Affinities for Detection of Pancreatic Cancer," Clin Cancer Res. Volume 18(3): pp. 839-849.
Li, et al., (2009) "Synthesis and characterization of a high-affinity αvβ6-specific ligand for in vitro and in vivo applications," Mol Cancer Ther. vol. 8(5) pp. 1239-1249.

* cited by examiner

*Primary Examiner* — Vanessa L. Ford
*Assistant Examiner* — Sandra Carter
(74) *Attorney, Agent, or Firm* — MCDONNELL BOEHNEN HULBERT & BERGHOFF LLP

(57) ABSTRACT

Alpha(v) beta (6) integrin (avb6) binding polypeptides are disclosed herein, and their use in treating and detecting tumors, and their use in treating pulmonary fibrosis.

11 Claims, 9 Drawing Sheets

Specification includes a Sequence Listing.

a.

b.

c.

f.

Loop1    Loop2

β₆    RGD-Loop    α'ᵥ e.

Score/Residue

−2.0

−2.5

−3.0

−3.5

0  1  2  3  4  5  6
R.M.S.D. to Design d.

g.

Ca(II)

Mg(II)

Ca(II)

h. β₆

LXXL motif i.

ASN37    ILE757    ARG61

ASP901    SER756 a.

b.

| Protein | BP Saturation (nM) | BP (nM) | av6_3 (nM) | av6_7 (nM) | av6_9 (nM) | av6_11 (nM) | av6_15 (nM) |
|---|---|---|---|---|---|---|---|
| $\alpha_v\beta_6$ | 2.3 | 2.6 | 2.6 | 89.8 | 37.5 | 8.1 | 9.3 |
| $\alpha_v\beta_8$ | 8.7 | 7.6 | 37.5 | 124 | 113 | 66.9 | 54.7 |
| X(selectivity) | 3.7 | 3 | 14 | 1.5 | 3 | 8 | 6 |

Sort1: 200pM of human αvβ6                    Sort2: 100pM of human
                                              αvβ6 + off rate selection

SEQUENCE LISTING

<160> NUMBER OF SEQ ID NOS: 36

<210> SEQ ID NO 1
<211> LENGTH: 72
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be A, C, D, E, F, G, I, K, L, M, R, S,
      T, V, W, or Y.

-continued

```
<220> FEATURE:
<221> NAME/KEY: MISC_FEATURE
<222> LOCATION: (2)..(2)
<223> OTHER INFORMATION: Xaa can be V, A, C, D, E, G, I, L, M, R, S, T,
      W, or Y.
<220> FEATURE:
<221> NAME/KEY: MISC_FEATURE
<222> LOCATION: (3)..(3)
<223> OTHER INFORMATION: Xaa can be V, A, C, D, F, G, I, L, N, or Q.
<220> FEATURE:
<221> NAME/KEY: MISC_FEATURE
<222> LOCATION: (4)..(4)
<223> OTHER INFORMATION: Xaa can be R, A, C, F, G, I, K, M, N, S, or V.
<220> FEATURE:
<221> NAME/KEY: MISC_FEATURE
<222> LOCATION: (5)..(5)
<223> OTHER INFORMATION: Xaa can be F, A, C, E, G, H, I, K, L, M, N, P,
      R, V, W, or Y.
<220> FEATURE:
<221> NAME/KEY: MISC_FEATURE
<222> LOCATION: (6)..(6)
<223> OTHER INFORMATION: Xaa can be V, A, D, G, H, I, K, L, M, N, Q, R,
      S, or T.
<220> FEATURE:
<221> NAME/KEY: MISC_FEATURE
<222> LOCATION: (7)..(7)
<223> OTHER INFORMATION: Xaa can be F, A, C, D, G, H, I, K, L, R, S, T,
      V, or Y.
<220> FEATURE:
<221> NAME/KEY: MISC_FEATURE
<222> LOCATION: (8)..(8)
<223> OTHER INFORMATION: Xaa can be R, E, G, I, K, S, T, or V.
<220> FEATURE:
<221> NAME/KEY: MISC_FEATURE
<222> LOCATION: (9)..(9)
<223> OTHER INFORMATION: Xaa can be G, C, D, R, or S.
<220> FEATURE:
<221> NAME/KEY: MISC_FEATURE
<222> LOCATION: (10)..(10)
<223> OTHER INFORMATION: Xaa can be D, A, E, H, V, or Y.
<220> FEATURE:
<221> NAME/KEY: MISC_FEATURE
<222> LOCATION: (11)..(11)
<223> OTHER INFORMATION: Xaa can be L, F, M, Q, or S.
<220> FEATURE:
<221> NAME/KEY: MISC_FEATURE
<222> LOCATION: (12)..(12)
<223> OTHER INFORMATION: Xaa can be A, E, G, K, P, R, S, T, or V.
<220> FEATURE:
<221> NAME/KEY: MISC_FEATURE
<222> LOCATION: (13)..(13)
<223> OTHER INFORMATION: Xaa can be E, A, D, F, G, H, I, K, L, M, N, P,
      Q, R, S, T, V, W, or Y.
<220> FEATURE:
<221> NAME/KEY: MISC_FEATURE
<222> LOCATION: (14)..(14)
<223> OTHER INFORMATION: Xaa can be L, E, F, K, M, R, S, or V.
<220> FEATURE:
<221> NAME/KEY: MISC_FEATURE
<222> LOCATION: (15)..(15)
<223> OTHER INFORMATION: Xaa can be M, A, C, E, G, H, I, K, L, N, P, Q,
      R, S, T, V, or W.
<220> FEATURE:
<221> NAME/KEY: MISC_FEATURE
<222> LOCATION: (16)..(16)
<223> OTHER INFORMATION: Xaa can be L, A, F, G, K, M, N, Q, R, S, T, V,
      or W.
<220> FEATURE:
<221> NAME/KEY: MISC_FEATURE
<222> LOCATION: (17)..(17)
<223> OTHER INFORMATION: Xaa can be R, C, G, K, M, S, or W.
<220> FEATURE:
<221> NAME/KEY: MISC_FEATURE
<222> LOCATION: (18)..(18)
<223> OTHER INFORMATION: Xaa can be A, E, F, G, H, I, S, T, V, W, or Y.
<220> FEATURE:
<221> NAME/KEY: MISC_FEATURE
<222> LOCATION: (19)..(19)
<223> OTHER INFORMATION: Xaa can be V, A, C, D, E, F, G, I, L, P, S, T,
```

-continued

```
      or W.
<220> FEATURE:
<221> NAME/KEY: MISC_FEATURE
<222> LOCATION: (20)..(20)
<223> OTHER INFORMATION: Xaa can be K, A, E, F, G, M, N, P, Q, R, S, T,
      or Y.
<220> FEATURE:
<221> NAME/KEY: MISC_FEATURE
<222> LOCATION: (21)..(21)
<223> OTHER INFORMATION: Xaa can be D, A, C, E, F, G, H, I, K, L, M, N,
      P, Q, R, S, T, V, W, or Y.
<220> FEATURE:
<221> NAME/KEY: MISC_FEATURE
<222> LOCATION: (22)..(22)
<223> OTHER INFORMATION: Xaa can be H, D, E, G, M, N, P, Q, R, V, W, or
      Y.
<220> FEATURE:
<221> NAME/KEY: MISC_FEATURE
<222> LOCATION: (23)..(23)
<223> OTHER INFORMATION: Xaa can be L, C, E, F, G, M, Q, S, V, or W.
<220> FEATURE:
<221> NAME/KEY: MISC_FEATURE
<222> LOCATION: (24)..(24)
<223> OTHER INFORMATION: Xaa can be K, C, G, M, N, Q, R, S, T, or W.
<220> FEATURE:
<221> NAME/KEY: MISC_FEATURE
<222> LOCATION: (25)..(25)
<223> OTHER INFORMATION: Xaa can be K, E, F, M, N, P, Q, R, S, or V.
<220> FEATURE:
<221> NAME/KEY: MISC_FEATURE
<222> LOCATION: (26)..(26)
<223> OTHER INFORMATION: Xaa can be E, C, D, G, K, N, Q, R, S, V, or W.
<220> FEATURE:
<221> NAME/KEY: MISC_FEATURE
<222> LOCATION: (27)..(27)
<223> OTHER INFORMATION: Xaa can be G, A, C, D, E, L, N, R, S, or V.
<220> FEATURE:
<221> NAME/KEY: MISC_FEATURE
<222> LOCATION: (28)..(28)
<223> OTHER INFORMATION: Xaa can be P, A, D, E, G, K, L, M, N, Q, R, S,
      T, or V.
<220> FEATURE:
<221> NAME/KEY: MISC_FEATURE
<222> LOCATION: (29)..(29)
<223> OTHER INFORMATION: Xaa can be H, A, C, D, E, G, I, K, L, M, N, P,
      Q, R, S, T, V, or Y.
<220> FEATURE:
<221> NAME/KEY: MISC_FEATURE
<222> LOCATION: (30)..(30)
<223> OTHER INFORMATION: Xaa can be W, C, D, G, I, L, R, S, or T.
<220> FEATURE:
<221> NAME/KEY: MISC_FEATURE
<222> LOCATION: (31)..(31)
<223> OTHER INFORMATION: Xaa can be N, A, D, E, F, G, H, I, K, L, M, R,
      S, V, W, or Y.
<220> FEATURE:
<221> NAME/KEY: MISC_FEATURE
<222> LOCATION: (32)..(32)
<223> OTHER INFORMATION: Xaa can be I, F, H, L, M, P, R, S, T, V, or W.
<220> FEATURE:
<221> NAME/KEY: MISC_FEATURE
<222> LOCATION: (33)..(33)
<223> OTHER INFORMATION: Xaa can be T, A, C, E, F, G, H, I, K, L, M, N,
      P, Q, R, S, V, W, or Y.
<220> FEATURE:
<221> NAME/KEY: MISC_FEATURE
<222> LOCATION: (34)..(34)
<223> OTHER INFORMATION: Xaa can be S, A, D, G, K, L, M, N, P, Q, R, T,
      V, or W.
<220> FEATURE:
<221> NAME/KEY: MISC_FEATURE
<222> LOCATION: (35)..(35)
<223> OTHER INFORMATION: Xaa can be T, A, F, G, I, K, L, N, P, Q, R, S,
      V, W, or Y.
<220> FEATURE:
<221> NAME/KEY: MISC_FEATURE
<222> LOCATION: (36)..(36)
<223> OTHER INFORMATION: Xaa can be N, A, D, E, G, I, K, L, P, Q, R, S,
      T, or V.
```

-continued

```
<220> FEATURE:
<221> NAME/KEY: MISC_FEATURE
<222> LOCATION: (37)..(37)
<223> OTHER INFORMATION: Xaa can be N, A, D, G, H, I, K, L, M, P, Q, R,
      S, T, V, W, or Y.
<220> FEATURE:
<221> NAME/KEY: MISC_FEATURE
<222> LOCATION: (38)..(38)
<223> OTHER INFORMATION: Xaa can be G, A, D, E, H, I, K, L, M, P, Q, R,
      S, T, V, or Y.
<220> FEATURE:
<221> NAME/KEY: MISC_FEATURE
<222> LOCATION: (39)..(39)
<223> OTHER INFORMATION: Xaa can be A, C, D, E, G, H, I, K, L, M, N, P,
      Q, R, S, T, V, W, or Y.
<220> FEATURE:
<221> NAME/KEY: MISC_FEATURE
<222> LOCATION: (40)..(40)
<223> OTHER INFORMATION: Xaa can be E, A, C, D, G, H, K, M, N, P, Q, R,
      S, T, V, W, or Y.
<220> FEATURE:
<221> NAME/KEY: MISC_FEATURE
<222> LOCATION: (41)..(41)
<223> OTHER INFORMATION: Xaa can be L, C, D, F, G, H, K, P, Q, R, S, V,
      or W.
<220> FEATURE:
<221> NAME/KEY: MISC_FEATURE
<222> LOCATION: (42)..(42)
<223> OTHER INFORMATION: Xaa can be V, A, D, E, F, G, I, K, L, M, R, S,
      W, or Y.
<220> FEATURE:
<221> NAME/KEY: MISC_FEATURE
<222> LOCATION: (43)..(43)
<223> OTHER INFORMATION: Xaa can be V, A, E, G, I, L, N, R, or T.
<220> FEATURE:
<221> NAME/KEY: MISC_FEATURE
<222> LOCATION: (44)..(44)
<223> OTHER INFORMATION: Xaa can be R, A, E, G, I, K, L, M, Q, S, T, or
      W.
<220> FEATURE:
<221> NAME/KEY: MISC_FEATURE
<222> LOCATION: (45)..(45)
<223> OTHER INFORMATION: Xaa can be G, A, C, D, E, K, L, M, N, Q, R, S,
      T, V, W, or Y.
<220> FEATURE:
<221> NAME/KEY: MISC_FEATURE
<222> LOCATION: (46)..(46)
<223> OTHER INFORMATION: Xaa can be I, A, C, E, F, G, L, M, N, S, T, or
      V.
<220> FEATURE:
<221> NAME/KEY: MISC_FEATURE
<222> LOCATION: (47)..(47)
<223> OTHER INFORMATION: Xaa can be H, A, D, E, F, G, I, K, L, M, N, P,
      Q, R, S, T, V, W, or Y.
<220> FEATURE:
<221> NAME/KEY: MISC_FEATURE
<222> LOCATION: (48)..(48)
<223> OTHER INFORMATION: Xaa can be E, A, C, D, G, H, K, L, N, P, Q, R,
      S, T, V, W, or Y.
<220> FEATURE:
<221> NAME/KEY: MISC_FEATURE
<222> LOCATION: (49)..(49)
<223> OTHER INFORMATION: Xaa can be S, A, D, E, F, G, H, I, K, L, N, P,
      R, T, V, or W.
<220> FEATURE:
<221> NAME/KEY: MISC_FEATURE
<222> LOCATION: (50)..(50)
<223> OTHER INFORMATION: Xaa can be D, A, E, F, G, I, K, N, Q, R, S, T,
      V, W, or Y.
<220> FEATURE:
<221> NAME/KEY: MISC_FEATURE
<222> LOCATION: (51)..(51)
<223> OTHER INFORMATION: Xaa can be A, E, G, R, S, T, V, or Y.
<220> FEATURE:
<221> NAME/KEY: MISC_FEATURE
<222> LOCATION: (52)..(52)
<223> OTHER INFORMATION: Xaa can be K, A, C, D, E, F, G, H, I, L, M, N,
      Q, R, S, T, V, or W.
<220> FEATURE:
```

```
<221> NAME/KEY: MISC_FEATURE
<222> LOCATION: (53)..(53)
<223> OTHER INFORMATION: Xaa can be R, A, C, D, E, G, H, I, L, M, N, Q,
      S, T, V, or W.
<220> FEATURE:
<221> NAME/KEY: MISC_FEATURE
<222> LOCATION: (54)..(54)
<223> OTHER INFORMATION: Xaa can be I, F, M, N, or T.
<220> FEATURE:
<221> NAME/KEY: MISC_FEATURE
<222> LOCATION: (55)..(55)
<223> OTHER INFORMATION: Xaa can be A, C, D, E, G, I, K, L, M, N, P, Q,
      R, S, T, V, W, or Y.
<220> FEATURE:
<221> NAME/KEY: MISC_FEATURE
<222> LOCATION: (56)..(56)
<223> OTHER INFORMATION: Xaa can be K, A, D, E, F, G, I, L, M, N, P, R,
      S, T, V, W, or Y.
<220> FEATURE:
<221> NAME/KEY: MISC_FEATURE
<222> LOCATION: (57)..(57)
<223> OTHER INFORMATION: Xaa can be W, A, C, F, G, H, I, L, M, Q, R, S,
      V, or Y.
<220> FEATURE:
<221> NAME/KEY: MISC_FEATURE
<222> LOCATION: (58)..(58)
<223> OTHER INFORMATION: Xaa can be V, A, C, D, E, G, K, L, M, Q, R, or
      S.
<220> FEATURE:
<221> NAME/KEY: MISC_FEATURE
<222> LOCATION: (59)..(59)
<223> OTHER INFORMATION: Xaa can be E, A, C, D, G, H, I, K, L, M, N, Q,
      R, S, T, V, or Y.
<220> FEATURE:
<221> NAME/KEY: MISC_FEATURE
<222> LOCATION: (60)..(60)
<223> OTHER INFORMATION: Xaa can be K, E, F, I, M, N, or R.
<220> FEATURE:
<221> NAME/KEY: MISC_FEATURE
<222> LOCATION: (61)..(61)
<223> OTHER INFORMATION: Xaa can be K, R, A, G, Q, S, or W.
<220> FEATURE:
<221> NAME/KEY: MISC_FEATURE
<222> LOCATION: (62)..(62)
<223> OTHER INFORMATION: Xaa can be F, C, G, I, L, S, V, W, or Y.
<220> FEATURE:
<221> NAME/KEY: MISC_FEATURE
<222> LOCATION: (63)..(63)
<223> OTHER INFORMATION: Xaa can be P, A, C, E, F, G, H, K, L, M, N, Q,
      R, S, T, or W.
<220> FEATURE:
<221> NAME/KEY: MISC_FEATURE
<222> LOCATION: (64)..(64)
<223> OTHER INFORMATION: Xaa can be G, A, C, D, E, F, H, I, K, L, M, N,
      P, Q, R, S, T, V, or W.
<220> FEATURE:
<221> NAME/KEY: MISC_FEATURE
<222> LOCATION: (65)..(65)
<223> OTHER INFORMATION: Xaa can be V, A, D, F, G, H, I, K, L, Q, R, S,
      or T.
<220> FEATURE:
<221> NAME/KEY: MISC_FEATURE
<222> LOCATION: (66)..(66)
<223> OTHER INFORMATION: Xaa can be H, A, C, D, F, G, K, L, N, Q, R, S,
      T, V, W, or Y.
<220> FEATURE:
<221> NAME/KEY: MISC_FEATURE
<222> LOCATION: (67)..(67)
<223> OTHER INFORMATION: Xaa can be T, C, I, K, L, N, R, S, V, or Y.
<220> FEATURE:
<221> NAME/KEY: MISC_FEATURE
<222> LOCATION: (68)..(68)
<223> OTHER INFORMATION: Xaa can be E, A, D, F, G, K, M, N, Q, R, S, T,
      W, or Y.
<220> FEATURE:
<221> NAME/KEY: MISC_FEATURE
<222> LOCATION: (69)..(69)
<223> OTHER INFORMATION: Xaa can be T, A, G, I, K, L, M, P, R, S, V, or
      W.
```

```
<220> FEATURE:
<221> NAME/KEY: MISC_FEATURE
<222> LOCATION: (70)..(70)
<223> OTHER INFORMATION: Xaa can be Q, E, H, I, M, R, S, or V.
<220> FEATURE:
<221> NAME/KEY: MISC_FEATURE
<222> LOCATION: (71)..(71)
<223> OTHER INFORMATION: Xaa can be Q, C, D, E, G, H, K, L, P, R, S, T,
      V, or W.
<220> FEATURE:
<221> NAME/KEY: MISC_FEATURE
<222> LOCATION: (72)..(72)
<223> OTHER INFORMATION: Xaa can be D, A, C, E, G, L, N, Q, R, S, V, or
      Y.

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa
65                  70

<210> SEQ ID NO 2
<211> LENGTH: 72
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be A, C, E , K, or T.
<220> FEATURE:
<221> NAME/KEY: MISC_FEATURE
<222> LOCATION: (2)..(2)
<223> OTHER INFORMATION: Xaa can be V, L, M, or R.
<220> FEATURE:
<221> NAME/KEY: MISC_FEATURE
<222> LOCATION: (4)..(4)
<223> OTHER INFORMATION: Xaa can be R or S.
<220> FEATURE:
<221> NAME/KEY: MISC_FEATURE
<222> LOCATION: (5)..(5)
<223> OTHER INFORMATION: Xaa can be F, G, K, L, M, or R.
<220> FEATURE:
<221> NAME/KEY: MISC_FEATURE
<222> LOCATION: (6)..(6)
<223> OTHER INFORMATION: Xaa can be V, A, K, or R.
<220> FEATURE:
<221> NAME/KEY: MISC_FEATURE
<222> LOCATION: (7)..(7)
<223> OTHER INFORMATION: Xaa can be F, A, G, K, or R.
<220> FEATURE:
<221> NAME/KEY: MISC_FEATURE
<222> LOCATION: (12)..(12)
<223> OTHER INFORMATION: Xaa can be A, G, K, or R.
<220> FEATURE:
<221> NAME/KEY: MISC_FEATURE
<222> LOCATION: (13)..(13)
<223> OTHER INFORMATION: Xaa can be E,  A, F, G, H, I, K, L, M, P, Q, R,
      S, T, V, W, or Y.
<220> FEATURE:
<221> NAME/KEY: MISC_FEATURE
<222> LOCATION: (14)..(14)
<223> OTHER INFORMATION: Xaa can be L or S.
<220> FEATURE:
<221> NAME/KEY: MISC_FEATURE
<222> LOCATION: (15)..(15)
```

-continued

```
<223> OTHER INFORMATION: Xaa can be M, K, L, R, or V.
<220> FEATURE:
<221> NAME/KEY: MISC_FEATURE
<222> LOCATION: (16)..(16)
<223> OTHER INFORMATION: Xaa can be L or R.
<220> FEATURE:
<221> NAME/KEY: MISC_FEATURE
<222> LOCATION: (18)..(18)
<223> OTHER INFORMATION: Xaa can be A, F, or V.
<220> FEATURE:
<221> NAME/KEY: MISC_FEATURE
<222> LOCATION: (19)..(19)
<223> OTHER INFORMATION: Xaa can be V, A, C, or S.
<220> FEATURE:
<221> NAME/KEY: MISC_FEATURE
<222> LOCATION: (20)..(20)
<223> OTHER INFORMATION: Xaa can be K or R.
<220> FEATURE:
<221> NAME/KEY: MISC_FEATURE
<222> LOCATION: (21)..(21)
<223> OTHER INFORMATION: Xaa can be D, A, F, G, H, R, S, T, V, W, or Y.
<220> FEATURE:
<221> NAME/KEY: MISC_FEATURE
<222> LOCATION: (23)..(23)
<223> OTHER INFORMATION: Xaa can be L or V.
<220> FEATURE:
<221> NAME/KEY: MISC_FEATURE
<222> LOCATION: (24)..(24)
<223> OTHER INFORMATION: Xaa can be K, G, or R.
<220> FEATURE:
<221> NAME/KEY: MISC_FEATURE
<222> LOCATION: (26)..(26)
<223> OTHER INFORMATION: Xaa can be E, R. or W.
<220> FEATURE:
<221> NAME/KEY: MISC_FEATURE
<222> LOCATION: (27)..(27)
<223> OTHER INFORMATION: Xaa can be G, L, or S.
<220> FEATURE:
<221> NAME/KEY: MISC_FEATURE
<222> LOCATION: (28)..(28)
<223> OTHER INFORMATION: Xaa can be P, K, M, or V.
<220> FEATURE:
<221> NAME/KEY: MISC_FEATURE
<222> LOCATION: (29)..(29)
<223> OTHER INFORMATION: Xaa can be H, G, L, N, R, or S.
<220> FEATURE:
<221> NAME/KEY: MISC_FEATURE
<222> LOCATION: (31)..(31)
<223> OTHER INFORMATION: Xaa can be N, R, S, or W.
<220> FEATURE:
<221> NAME/KEY: MISC_FEATURE
<222> LOCATION: (32)..(32)
<223> OTHER INFORMATION: Xaa can be I, F, or W.
<220> FEATURE:
<221> NAME/KEY: MISC_FEATURE
<222> LOCATION: (33)..(33)
<223> OTHER INFORMATION: Xaa can be T, F, G, R, S, V, W, or Y.
<220> FEATURE:
<221> NAME/KEY: MISC_FEATURE
<222> LOCATION: (34)..(34)
<223> OTHER INFORMATION: Xaa can be S, G, K, or R.
<220> FEATURE:
<221> NAME/KEY: MISC_FEATURE
<222> LOCATION: (35)..(35)
<223> OTHER INFORMATION: Xaa can be T, A, G, I, P, or S.
<220> FEATURE:
<221> NAME/KEY: MISC_FEATURE
<222> LOCATION: (36)..(36)
<223> OTHER INFORMATION: Xaa can be N, A, G, R, or V.
<220> FEATURE:
<221> NAME/KEY: MISC_FEATURE
<222> LOCATION: (37)..(37)
<223> OTHER INFORMATION: Xaa can be N, A, G, L, R, S, T, V, or W.
<220> FEATURE:
<221> NAME/KEY: MISC_FEATURE
<222> LOCATION: (38)..(38)
<223> OTHER INFORMATION: Xaa can be G, A, K, R, or S.
<220> FEATURE:
<221> NAME/KEY: MISC_FEATURE
```

-continued

```
<222> LOCATION: (39)..(39)
<223> OTHER INFORMATION: Xaa can be A, G, H, K, L, N, P, R, S, T, or V.
<220> FEATURE:
<221> NAME/KEY: MISC_FEATURE
<222> LOCATION: (40)..(40)
<223> OTHER INFORMATION: Xaa can be E, A, G, Q, R, S, or T.
<220> FEATURE:
<221> NAME/KEY: MISC_FEATURE
<222> LOCATION: (42)..(42)
<223> OTHER INFORMATION: Xaa can be V or F.
<220> FEATURE:
<221> NAME/KEY: MISC_FEATURE
<222> LOCATION: (44)..(44)
<223> OTHER INFORMATION: Xaa can be R or K.
<220> FEATURE:
<221> NAME/KEY: MISC_FEATURE
<222> LOCATION: (45)..(45)
<223> OTHER INFORMATION: Xaa can be G, R, or S.
<220> FEATURE:
<221> NAME/KEY: MISC_FEATURE
<222> LOCATION: (46)..(46)
<223> OTHER INFORMATION: Xaa can be I or V.
<220> FEATURE:
<221> NAME/KEY: MISC_FEATURE
<222> LOCATION: (47)..(47)
<223> OTHER INFORMATION: Xaa can be H, G, P, R, or V.
<220> FEATURE:
<221> NAME/KEY: MISC_FEATURE
<222> LOCATION: (48)..(48)
<223> OTHER INFORMATION: Xaa can be E, A, G, H, K, L, or R.
<220> FEATURE:
<221> NAME/KEY: MISC_FEATURE
<222> LOCATION: (49)..(49)
<223> OTHER INFORMATION: Xaa can be S, D, F, I, R, or W.
<220> FEATURE:
<221> NAME/KEY: MISC_FEATURE
<222> LOCATION: (50)..(50)
<223> OTHER INFORMATION: Xaa can be D, E, G, or S.
<220> FEATURE:
<221> NAME/KEY: MISC_FEATURE
<222> LOCATION: (52)..(52)
<223> OTHER INFORMATION: Xaa can be K, D, F, N, Q, R, S, T, or V.
<220> FEATURE:
<221> NAME/KEY: MISC_FEATURE
<222> LOCATION: (53)..(53)
<223> OTHER INFORMATION: Xaa can be R, A, D, M, Q, or V.
<220> FEATURE:
<221> NAME/KEY: MISC_FEATURE
<222> LOCATION: (55)..(55)
<223> OTHER INFORMATION: Xaa can be A, E, G, S, or T.
<220> FEATURE:
<221> NAME/KEY: MISC_FEATURE
<222> LOCATION: (56)..(56)
<223> OTHER INFORMATION: Xaa can be K, A, G, N, or R.
<220> FEATURE:
<221> NAME/KEY: MISC_FEATURE
<222> LOCATION: (57)..(57)
<223> OTHER INFORMATION: Xaa can be W, G, or Y.
<220> FEATURE:
<221> NAME/KEY: MISC_FEATURE
<222> LOCATION: (58)..(58)
<223> OTHER INFORMATION: Xaa can be V or K.
<220> FEATURE:
<221> NAME/KEY: MISC_FEATURE
<222> LOCATION: (59)..(59)
<223> OTHER INFORMATION: Xaa can be E, A, G, K, L, Q, R, S, T, or V.
<220> FEATURE:
<221> NAME/KEY: MISC_FEATURE
<222> LOCATION: (60)..(60)
<223> OTHER INFORMATION: Xaa can be K, I, M, or  N.
<220> FEATURE:
<221> NAME/KEY: MISC_FEATURE
<222> LOCATION: (62)..(62)
<223> OTHER INFORMATION: Xaa can be F or W.
<220> FEATURE:
<221> NAME/KEY: MISC_FEATURE
<222> LOCATION: (63)..(63)
<223> OTHER INFORMATION: Xaa can be P, F, G, K, L, R, or S.
<220> FEATURE:
```

-continued

```
<221> NAME/KEY: MISC_FEATURE
<222> LOCATION: (64)..(64)
<223> OTHER INFORMATION: Xaa can be G, Q, R, S, T, or V.
<220> FEATURE:
<221> NAME/KEY: MISC_FEATURE
<222> LOCATION: (65)..(65)
<223> OTHER INFORMATION: Xaa can be V or T.
<220> FEATURE:
<221> NAME/KEY: MISC_FEATURE
<222> LOCATION: (66)..(66)
<223> OTHER INFORMATION: Xaa can be H, G, Q, or R.
<220> FEATURE:
<221> NAME/KEY: MISC_FEATURE
<222> LOCATION: (68)..(68)
<223> OTHER INFORMATION: Xaa can be E or R.
<220> FEATURE:
<221> NAME/KEY: MISC_FEATURE
<222> LOCATION: (70)..(70)
<223> OTHER INFORMATION: Xaa can be Q or R.
<220> FEATURE:
<221> NAME/KEY: MISC_FEATURE
<222> LOCATION: (71)..(71)
<223> OTHER INFORMATION: Xaa can be Q, T, or V.

<400> SEQUENCE: 2

Xaa Xaa Val Xaa Xaa Xaa Xaa Arg Gly Asp Leu Xaa Xaa Xaa Xaa Xaa
1               5                   10                  15

Arg Xaa Xaa Xaa Xaa His Xaa Xaa Lys Xaa Xaa Xaa Xaa Trp Xaa Xaa
            20                  25                  30

Xaa Xaa Xaa Xaa Xaa Xaa Xaa Xaa Leu Xaa Val Xaa Xaa Xaa Xaa Xaa
        35                  40                  45

Xaa Xaa Ala Xaa Xaa Ile Xaa Xaa Xaa Xaa Xaa Xaa Arg Xaa Xaa Xaa
    50                  55                  60

Xaa Xaa Thr Xaa Thr Xaa Xaa Asp
65                  70

<210> SEQ ID NO 3
<211> LENGTH: 72
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be C, A, or K.
<220> FEATURE:
<221> NAME/KEY: MISC_FEATURE
<222> LOCATION: (2)..(2)
<223> OTHER INFORMATION: Xaa can be V, L, or R.
<220> FEATURE:
<221> NAME/KEY: MISC_FEATURE
<222> LOCATION: (5)..(5)
<223> OTHER INFORMATION: Xaa can be F, G, M, or R.
<220> FEATURE:
<221> NAME/KEY: MISC_FEATURE
<222> LOCATION: (6)..(6)
<223> OTHER INFORMATION: Xaa can be V or R.
<220> FEATURE:
<221> NAME/KEY: MISC_FEATURE
<222> LOCATION: (7)..(7)
<223> OTHER INFORMATION: Xaa can be F, G, or R.
<220> FEATURE:
<221> NAME/KEY: MISC_FEATURE
<222> LOCATION: (12)..(12)
<223> OTHER INFORMATION: Xaa can be A, G, or K.
<220> FEATURE:
<221> NAME/KEY: MISC_FEATURE
<222> LOCATION: (13)..(13)
<223> OTHER INFORMATION: Xaa can be E, A, F, G, H, I, L, P, R, S, T, V,
      W, or Y.
<220> FEATURE:
<221> NAME/KEY: MISC_FEATURE
```

-continued

```
<222> LOCATION: (14)..(14)
<223> OTHER INFORMATION: Xaa can be L or S.
<220> FEATURE:
<221> NAME/KEY: MISC_FEATURE
<222> LOCATION: (15)..(15)
<223> OTHER INFORMATION: Xaa can be M, K, R, or V.
<220> FEATURE:
<221> NAME/KEY: MISC_FEATURE
<222> LOCATION: (18)..(18)
<223> OTHER INFORMATION: Xaa can be A or V.
<220> FEATURE:
<221> NAME/KEY: MISC_FEATURE
<222> LOCATION: (19)..(19)
<223> OTHER INFORMATION: Xaa can be V, A, or S.
<220> FEATURE:
<221> NAME/KEY: MISC_FEATURE
<222> LOCATION: (21)..(21)
<223> OTHER INFORMATION: Xaa can be D, A, F, G, R, S, or W.
<220> FEATURE:
<221> NAME/KEY: MISC_FEATURE
<222> LOCATION: (23)..(23)
<223> OTHER INFORMATION: Xaa can be L or V.
<220> FEATURE:
<221> NAME/KEY: MISC_FEATURE
<222> LOCATION: (24)..(24)
<223> OTHER INFORMATION: Xaa can be K, G, or R.
<220> FEATURE:
<221> NAME/KEY: MISC_FEATURE
<222> LOCATION: (26)..(26)
<223> OTHER INFORMATION: Xaa can be E or R.
<220> FEATURE:
<221> NAME/KEY: MISC_FEATURE
<222> LOCATION: (28)..(28)
<223> OTHER INFORMATION: Xaa can be P, K, or V.
<220> FEATURE:
<221> NAME/KEY: MISC_FEATURE
<222> LOCATION: (31)..(31)
<223> OTHER INFORMATION: Xaa can be N, R, or S.
<220> FEATURE:
<221> NAME/KEY: MISC_FEATURE
<222> LOCATION: (32)..(32)
<223> OTHER INFORMATION: Xaa can be I or W.
<220> FEATURE:
<221> NAME/KEY: MISC_FEATURE
<222> LOCATION: (33)..(33)
<223> OTHER INFORMATION: Xaa can be T, G, R, or V.
<220> FEATURE:
<221> NAME/KEY: MISC_FEATURE
<222> LOCATION: (34)..(34)
<223> OTHER INFORMATION: Xaa can be S, G, K, or R.
<220> FEATURE:
<221> NAME/KEY: MISC_FEATURE
<222> LOCATION: (35)..(35)
<223> OTHER INFORMATION: Xaa can be T, A, or G.
<220> FEATURE:
<221> NAME/KEY: MISC_FEATURE
<222> LOCATION: (36)..(36)
<223> OTHER INFORMATION: Xaa can be N, G, R, or V.
<220> FEATURE:
<221> NAME/KEY: MISC_FEATURE
<222> LOCATION: (37)..(37)
<223> OTHER INFORMATION: Xaa can be N, G, R, T, V, or W.
<220> FEATURE:
<221> NAME/KEY: MISC_FEATURE
<222> LOCATION: (38)..(38)
<223> OTHER INFORMATION: Xaa can be G, A, K, R, or S.
<220> FEATURE:
<221> NAME/KEY: MISC_FEATURE
<222> LOCATION: (39)..(39)
<223> OTHER INFORMATION: Xaa can be A, G, H, K, P, R, S, or V.
<220> FEATURE:
<221> NAME/KEY: MISC_FEATURE
<222> LOCATION: (40)..(40)
<223> OTHER INFORMATION: Xaa can be E, G, R, or S.
<220> FEATURE:
<221> NAME/KEY: MISC_FEATURE
<222> LOCATION: (45)..(45)
<223> OTHER INFORMATION: Xaa can be G or R.
<220> FEATURE:
```

```
<221> NAME/KEY: MISC_FEATURE
<222> LOCATION: (47)..(47)
<223> OTHER INFORMATION: Xaa can be H, R, or V.
<220> FEATURE:
<221> NAME/KEY: MISC_FEATURE
<222> LOCATION: (48)..(48)
<223> OTHER INFORMATION: Xaa can be E, H, or L.
<220> FEATURE:
<221> NAME/KEY: MISC_FEATURE
<222> LOCATION: (49)..(49)
<223> OTHER INFORMATION: Xaa can be S, F, I, or R.
<220> FEATURE:
<221> NAME/KEY: MISC_FEATURE
<222> LOCATION: (50)..(50)
<223> OTHER INFORMATION: Xaa can be D or E.
<220> FEATURE:
<221> NAME/KEY: MISC_FEATURE
<222> LOCATION: (52)..(52)
<223> OTHER INFORMATION: Xaa can be K, N, or S.
<220> FEATURE:
<221> NAME/KEY: MISC_FEATURE
<222> LOCATION: (53)..(53)
<223> OTHER INFORMATION: Xaa can be R, A, D, or Q.
<220> FEATURE:
<221> NAME/KEY: MISC_FEATURE
<222> LOCATION: (55)..(55)
<223> OTHER INFORMATION: Xaa can be A, E, G, S, or T.
<220> FEATURE:
<221> NAME/KEY: MISC_FEATURE
<222> LOCATION: (56)..(56)
<223> OTHER INFORMATION: Xaa can be K, A, G, N, or R.
<220> FEATURE:
<221> NAME/KEY: MISC_FEATURE
<222> LOCATION: (57)..(57)
<223> OTHER INFORMATION: Xaa can be W or Y.
<220> FEATURE:
<221> NAME/KEY: MISC_FEATURE
<222> LOCATION: (59)..(59)
<223> OTHER INFORMATION: Xaa can be E, A, G, K, L, R, T, or V.
<220> FEATURE:
<221> NAME/KEY: MISC_FEATURE
<222> LOCATION: (60)..(60)
<223> OTHER INFORMATION: Xaa can be K or I.
<220> FEATURE:
<221> NAME/KEY: MISC_FEATURE
<222> LOCATION: (62)..(62)
<223> OTHER INFORMATION: Xaa can be F or W.
<220> FEATURE:
<221> NAME/KEY: MISC_FEATURE
<222> LOCATION: (63)..(63)
<223> OTHER INFORMATION: Xaa can be P, G, K, R, or S.
<220> FEATURE:
<221> NAME/KEY: MISC_FEATURE
<222> LOCATION: (64)..(64)
<223> OTHER INFORMATION: Xaa can be G, Q, R, S, T, or V.
<220> FEATURE:
<221> NAME/KEY: MISC_FEATURE
<222> LOCATION: (66)..(66)
<223> OTHER INFORMATION: Xaa can be H, G, Q, or R.
<220> FEATURE:
<221> NAME/KEY: MISC_FEATURE
<222> LOCATION: (68)..(68)
<223> OTHER INFORMATION: Xaa can be E or R.
<220> FEATURE:
<221> NAME/KEY: MISC_FEATURE
<222> LOCATION: (71)..(71)
<223> OTHER INFORMATION: Xaa can be Q, T, or V.

<400> SEQUENCE: 3

Xaa Xaa Val Arg Xaa Xaa Xaa Arg Gly Asp Leu Xaa Xaa Xaa Xaa Leu
1               5                   10                  15

Arg Xaa Xaa Lys Xaa His Xaa Xaa Lys Xaa Gly Xaa His Trp Xaa Xaa
            20                  25                  30

Xaa Xaa Xaa Xaa Xaa Xaa Xaa Xaa Leu Val Val Arg Xaa Ile Xaa Xaa
        35                  40                  45
```

-continued

```
Xaa Xaa Ala Xaa Xaa Ile Xaa Xaa Xaa Val Xaa Xaa Arg Xaa Xaa Xaa
    50                  55                  60

Val Xaa Thr Xaa Thr Gln Xaa Asp
65                  70

<210> SEQ ID NO 4
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 4

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Thr Asn Asn Gly Ala Glu Leu Val Val Arg Gly Ile His
        35                  40                  45

Glu Ser Asp Ala Lys Arg Ile Ala Arg Thr Val Glu Lys Leu Thr Asn
    50                  55                  60

Gly Lys Ser Gln Ser Leu Val Leu Thr
65                  70

<210> SEQ ID NO 5
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 5

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Thr Asn Asn Gly Ala Glu Leu Val Val Arg Gly Ile His
        35                  40                  45

Glu Ser Asp Ala Lys Arg Ile Ala Asn Trp Ala Lys Thr Tyr Ser Pro
    50                  55                  60

Gly Gly Lys Glu Ser Tyr Thr Ile Pro
65                  70

<210> SEQ ID NO 6
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 6

Met Ala Val Val Arg Phe Val Phe Arg Gly Asp Leu Ala Glu Leu Met
```

```
1               5                    10                   15

Leu Arg Ala Val Lys Asp His Leu Lys Lys Glu Gly Pro His Trp Asn
            20                   25                   30

Ile Thr Ser Thr Asn Asn Gly Ala Glu Leu Val Val Arg Gly Ile His
        35                   40                   45

Glu Ser Asp Ala Lys Arg Ile Ala Lys Trp Val Glu Lys Arg Phe Pro
    50                   55                   60

Gly Val His Thr Glu Thr Gln Gln Asp
65                   70
```

```
<210> SEQ ID NO 7
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 7
```

```
Met Ala Val Val Arg Phe Val Phe Arg Gly Asp Leu Ala Glu Leu Met
1               5                    10                   15

Leu Arg Ala Val Lys Asp His Leu Lys Lys Glu Gly Pro His Trp Asn
            20                   25                   30

Ile Thr Ser Thr Asn Asn Gly Ala Glu Leu Val Val Arg Gly Ile His
        35                   40                   45

Glu Ser Asp Ala Lys Arg Ile Ala Lys Trp Ala Arg Leu Lys Phe Pro
    50                   55                   60

Gly Thr Asp Thr Arg Ile Glu Val Arg
65                   70
```

```
<210> SEQ ID NO 8
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 8
```

```
Met Ala Val Val Arg Phe Val Phe Arg Gly Asp Leu Ala Glu Leu Met
1               5                    10                   15

Leu Arg Ala Val Lys Asp His Leu Lys Lys Glu Gly Pro His Trp Asn
            20                   25                   30

Ile Thr Ser Asp Glu Ser Gly Phe Glu Leu Val Val Arg Gly Ile His
        35                   40                   45

Glu Ser Asp Ala Lys Arg Ile Ala Arg Thr Val Glu Lys Leu Thr Asn
    50                   55                   60

Gly Lys Ser Gln Ser Leu Val Leu Thr
65                   70
```

```
<210> SEQ ID NO 9
<211> LENGTH: 73
<212> TYPE: PRT
<213> ORGANISM: Artificial Sequence
<220> FEATURE:
<223> OTHER INFORMATION: Synthetic peptide
```

-continued

```
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 9

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Asp Glu Ser Gly Phe Glu Leu Val Val Arg Gly Ile His
        35                  40                  45

Glu Ser Asp Ala Lys Arg Ile Ala Asn Trp Ala Lys Thr Tyr Ser Pro
    50                  55                  60

Gly Gly Lys Glu Ser Tyr Thr Ile Pro
65                  70

<210> SEQ ID NO 10
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 10

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Asp Glu Ser Gly Phe Glu Leu Val Val Arg Gly Ile His
        35                  40                  45

Glu Ser Asp Ala Lys Arg Ile Ala Lys Trp Val Glu Lys Arg Phe Pro
    50                  55                  60

Gly Val His Thr Glu Thr Gln Gln Asp
65                  70

<210> SEQ ID NO 11
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 11

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Asp Glu Ser Gly Phe Glu Leu Val Val Arg Gly Ile His
        35                  40                  45

Glu Ser Asp Ala Lys Arg Ile Ala Lys Trp Ala Arg Leu Lys Phe Pro
    50                  55                  60

Gly Thr Asp Thr Arg Ile Glu Val Arg
65                  70
```

```
<210> SEQ ID NO 12
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 12

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Asp Thr Ser Lys Gly Ala Glu Leu Val Val Arg Gly Ile
        35                  40                  45

His Glu Ser Asp Ala Lys Arg Ile Ala Arg Thr Val Glu Lys Leu Thr
    50                  55                  60

Asn Gly Lys Ser Gln Ser Leu Val Leu
65                  70

<210> SEQ ID NO 13
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 13

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Asp Thr Ser Lys Gly Ala Glu Leu Val Val Arg Gly Ile
        35                  40                  45

His Glu Ser Asp Ala Lys Arg Ile Ala Asn Trp Ala Lys Thr Tyr Ser
    50                  55                  60

Pro Gly Gly Lys Glu Ser Tyr Thr Ile
65                  70

<210> SEQ ID NO 14
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 14

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30
```

-continued

```
Ile Thr Ser Asp Thr Ser Lys Gly Ala Glu Leu Val Val Arg Gly Ile
        35                  40                  45

His Glu Ser Asp Ala Lys Arg Ile Ala Lys Trp Val Glu Lys Arg Phe
    50                  55                  60

Pro Gly Val His Thr Glu Thr Gln Gln
65                  70

<210> SEQ ID NO 15
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 15

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
                20                  25                  30

Ile Thr Ser Asp Thr Ser Lys Gly Ala Glu Leu Val Val Arg Gly Ile
        35                  40                  45

His Glu Ser Asp Ala Lys Arg Ile Ala Lys Trp Ala Arg Leu Lys Phe
    50                  55                  60

Pro Gly Thr Asp Thr Arg Ile Glu Val
65                  70

<210> SEQ ID NO 16
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 16

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
                20                  25                  30

Ile Thr Ser Val Glu Ser Ser Gln Val Glu Leu Val Val Arg Gly Ile
        35                  40                  45

His Glu Ser Asp Ala Lys Arg Ile Ala Arg Thr Val Glu Lys Leu Thr
    50                  55                  60

Asn Gly Lys Ser Gln Ser Leu Val Leu
65                  70

<210> SEQ ID NO 17
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.
```

-continued

```
<400> SEQUENCE: 17

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Val Glu Ser Ser Gln Val Glu Leu Val Val Arg Gly Ile
        35                  40                  45

His Glu Ser Asp Ala Lys Arg Ile Ala Asn Trp Ala Lys Thr Tyr Ser
    50                  55                  60

Pro Gly Gly Lys Glu Ser Tyr Thr Ile
65              70

<210> SEQ ID NO 18
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 18

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Val Glu Ser Ser Gln Val Glu Leu Val Val Arg Gly Ile
        35                  40                  45

His Glu Ser Asp Ala Lys Arg Ile Ala Lys Trp Val Glu Lys Arg Phe
    50                  55                  60

Pro Gly Val His Thr Glu Thr Gln Gln
65              70

<210> SEQ ID NO 19
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 19

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Val Glu Ser Ser Gln Val Glu Leu Val Val Arg Gly Ile
        35                  40                  45

His Glu Ser Asp Ala Lys Arg Ile Ala Lys Trp Ala Arg Leu Lys Phe
    50                  55                  60

Pro Gly Thr Asp Thr Arg Ile Glu Val
65              70

<210> SEQ ID NO 20
<211> LENGTH: 73
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 20

Met Ala Val Val Arg Phe Val Phe Arg Gly Asp Leu Ala Glu Leu Arg
1               5                   10                  15

Leu Arg Ala Val Lys Asp His Leu Lys Lys Glu Gly Pro His Trp Asn
            20                  25                  30

Ile Thr Ser Thr Asn Asn Gly Ala Glu Leu Val Val Arg Gly Ile His
        35                  40                  45

Glu Ser Asp Ala Lys Arg Ile Ala Lys Trp Val Glu Lys Arg Phe Pro
    50                  55                  60

Gly Val His Thr Glu Thr Gln Gln Asp
65                  70

<210> SEQ ID NO 21
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 21

Met Ala Val Val Arg Phe Val Phe Arg Gly Asp Leu Ala Thr Leu Met
1               5                   10                  15

Leu Arg Ala Val Lys Asp His Leu Lys Lys Glu Gly Pro His Trp Asn
            20                  25                  30

Ile Thr Ser Thr Asn Asn Gly Ala Glu Leu Val Val Arg Gly Ile His
        35                  40                  45

Glu Ser Asp Ala Lys Arg Ile Ala Lys Trp Val Glu Lys Arg Phe Pro
    50                  55                  60

Gly Val His Thr Glu Thr Gln Gln Asp
65                  70

<210> SEQ ID NO 22
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 22

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Thr Asn Asn Gly Lys Glu Leu Val Val Arg Gly Ile His
        35                  40                  45

Glu Ser Asp Ala Lys Arg Ile Ala Lys Trp Val Glu Lys Arg Phe Pro
    50                  55                  60
```

```
Gly Val His Thr Glu Thr Gln Gln Asp
65                  70

<210> SEQ ID NO 23
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 23

Met Ala Val Val Arg Phe Val Phe Arg Gly Asp Leu Ala Glu Leu Met
1               5                   10                  15

Leu Arg Ala Val Lys Asp His Leu Lys Lys Glu Gly Pro His Trp Asn
            20                  25                  30

Ile Thr Ser Thr Asn Asn Gly Ala Glu Leu Val Val Arg Gly Ile His
        35                  40                  45

Glu Ser Asp Ala Lys Arg Ile Ala Lys Trp Val Glu Lys Arg Phe Pro
    50                  55                  60

Arg Val His Thr Glu Thr Gln Gln Asp
65                  70

<210> SEQ ID NO 24
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 24

Met Ala Val Val Arg Phe Val Phe Arg Gly Asp Leu Ala Glu Leu Arg
1               5                   10                  15

Leu Arg Ala Val Lys Asp His Leu Lys Lys Glu Gly Pro His Trp Asn
            20                  25                  30

Ile Thr Ser Thr Asn Asn Gly Ala Glu Leu Val Val Arg Gly Ile His
        35                  40                  45

Glu Ser Asp Ala Lys Arg Ile Ala Lys Trp Val Glu Lys Arg Phe Pro
    50                  55                  60

Arg Val His Thr Glu Thr Gln Gln Asp
65                  70

<210> SEQ ID NO 25
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 25

Met Ala Val Val Arg Phe Val Phe Arg Gly Asp Leu Ala Glu Leu Met
1               5                   10                  15
```

```
Leu Arg Ala Val Lys Asp His Leu Lys Lys Glu Gly Pro His Trp Asn
            20                  25                  30

Ile Thr Ser Thr Asn Asn Gly Lys Glu Leu Val Val Arg Gly Ile His
        35                  40                  45

Glu Ser Asp Ala Lys Arg Ile Ala Lys Trp Val Glu Lys Arg Phe Pro
    50                  55                  60

Arg Val His Thr Glu Thr Gln Gln Asp
65                  70

<210> SEQ ID NO 26
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 26

Met Ala Val Val Arg Phe Val Phe Arg Gly Asp Leu Ala Thr Leu Met
1               5                   10                  15

Leu Arg Ala Val Lys Asp His Leu Lys Lys Glu Gly Pro His Trp Asn
            20                  25                  30

Ile Thr Ser Thr Asn Asn Gly Ala Glu Leu Val Val Arg Gly Ile His
        35                  40                  45

Glu Ser Asp Ala Lys Arg Ile Ala Lys Trp Val Glu Lys Arg Phe Pro
    50                  55                  60

Arg Val His Thr Glu Thr Gln Gln Asp
65                  70

<210> SEQ ID NO 27
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 27

Met Ala Val Val Arg Phe Val Phe Arg Gly Asp Leu Ala Thr Leu Arg
1               5                   10                  15

Leu Arg Ala Val Lys Asp His Leu Lys Lys Glu Gly Pro His Trp Asn
            20                  25                  30

Ile Thr Ser Thr Asn Asn Gly Lys Glu Leu Val Val Arg Gly Ile His
        35                  40                  45

Glu Ser Asp Ala Lys Arg Ile Ala Lys Trp Val Glu Lys Arg Phe Pro
    50                  55                  60

Gly Val His Thr Glu Thr Gln Gln Asp
65                  70

<210> SEQ ID NO 28
<211> LENGTH: 73
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

-continued

```
<222> LOCATION: (1)..(1)
<223> OTHER INFORMATION: Optional N-terminal methionine residue.

<400> SEQUENCE: 28

Met Ala Val Val Arg Phe Val Phe Arg Gly Asp Leu Ala Thr Leu Arg
1               5                   10                  15

Leu Arg Ala Val Lys Asp His Leu Lys Lys Glu Gly Pro His Trp Asn
            20                  25                  30

Ile Thr Ser Thr Asn Asn Gly Lys Glu Leu Val Val Arg Gly Ile His
        35                  40                  45

Glu Ser Asp Ala Lys Arg Ile Ala Lys Trp Val Glu Lys Arg Phe Pro
    50                  55                  60

Arg Val His Thr Glu Thr Gln Gln Asp
65                  70

<210> SEQ ID NO 29
<211> LENGTH: 75
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 29

Met Thr Lys Cys Val Val Arg Phe Val Phe Arg Gly Asp Leu Ala Thr
1               5                   10                  15

Leu Met Leu Arg Ala Val Lys Asp His Leu Lys Lys Glu Gly Pro His
            20                  25                  30

Trp Asn Ile Thr Ser Thr Asn Asn Gly Ala Glu Leu Val Val Arg Gly
        35                  40                  45

Ile His Glu Ser Asp Ala Lys Arg Ile Ala Lys Trp Val Glu Lys Arg
    50                  55                  60

Phe Pro Gly Val His Thr Glu Thr Gln Cys Asp
65                  70                  75

<210> SEQ ID NO 30
<211> LENGTH: 75
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional N-terminal methionine residue.

<400> SEQUENCE: 30

Met Thr Lys Cys Val Val Arg Phe Val Phe Arg Gly Asp Leu Ala Glu
1               5                   10                  15

Leu Met Leu Arg Ala Val Lys Asp His Leu Lys Lys Glu Gly Pro His
            20                  25                  30

Trp Asn Ile Thr Ser Thr Asn Asn Gly Lys Glu Leu Val Val Arg Gly
        35                  40                  45

Ile His Glu Ser Asp Ala Lys Arg Ile Ala Lys Trp Val Glu Lys Arg
    50                  55                  60

Phe Pro Arg Val His Thr Glu Thr Gln Cys Asp
65                  70                  75
```

```
<210> SEQ ID NO 31
<211> LENGTH: 8
<212> TYPE: PRT
<213> ORGANISM: Artificial Sequence
<220> FEATURE:
<223> OTHER INFORMATION: Synthetic peptide

<400> SEQUENCE: 31

Arg Gly Asp Leu Gly Ala Leu Ala
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 32

Arg Gly Asp Leu Xaa Xaa Leu
1               5

<210> SEQ ID NO 33
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 33

Leu Xaa Xaa Leu
1

<210> SEQ ID NO 34
<211> LENGTH: 15
<212> TYPE: PRT
<213> ORGANISM: Artificial Sequence
<220> FEATURE:
<223> OTHER INFORMATION: Synthetic peptide

<400> SEQUENCE: 34

Gly Leu Asn Asp Ile Phe Glu Ala Gln Lys Ile Glu Trp His Glu
1               5                   10                  15

<210> SEQ ID NO 35
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can be G or R.
<220> FEATURE:
<221> NAME/KEY: MISC_FEATURE
<222> LOCATION: (4)..(4)
<223> OTHER INFORMATION: Xaa can be V or T.
<220> FEATURE:
<221> NAME/KEY: MISC_FEATURE
<222> LOCATION: (5)..(5)
<223> OTHER INFORMATION: Xaa can be H, A, C, D, F, G, K, L, N, Q, R, S,
      T, V, W, or Y.
```

-continued

```
<400> SEQUENCE: 35

Phe Pro Xaa Xaa Xaa Thr
1               5

<210> SEQ ID NO 36
<211> LENGTH: 65
<212> TYPE: PRT
<213> ORGANISM: Artificial Sequence
<220> FEATURE:
<223> OTHER INFORMATION: Synthetic peptide

<400> SEQUENCE: 36

Ala Glu Val Arg Phe Val Phe Arg Gly Asp Leu Thr Glu Leu Met Leu
1               5                   10                  15

Arg Ala Val Lys Asp His Leu Lys Lys Glu Gly Pro His Trp Asn Ile
            20                  25                  30

Thr Ser Arg Gly Asn Glu Leu Glu Val Arg Gly Ser His Glu Ser Asp
        35                  40                  45

Ala Lys Arg Ile Gln Lys Glu Phe Pro Ser Val Gln Ser Thr Thr Gln
    50                  55                  60

Ala
65
```

COMPUTATIONAL DESIGN OF ALPHA(V) BETA (6) INTEGRIN BINDING PROTEINS

CROSS REFERENCE

This application is a U.S. National Phase of International Application No. PCT/US2020/057016, filed Oct. 23, 2020, which claims priority to U.S. Provisional Application No. 62/925,868, filed Oct. 25, 2019, both of which are incorporated by reference herein in their entirety.

FEDERAL FUNDING STATEMENT

This invention was made with government support under Grant No. RO1 GM092802, awarded by the National Institutes of Health. The government has certain rights in the invention.

SEQUENCE LISTING STATEMENT

A computer readable form of the Sequence Listing is filed with this application by electronic submission and is incorporated into this application by reference in its entirety. The Sequence Listing is contained in the file created on Oct. 21, 2020, having the file name "19-1733-PCT_Sequence-Listing_ST25.txt" and is 42 kb in size.

BACKGROUND

Integrins are class of heterodimeric cell surface proteins involved in a wide range of cellular functions including cell-cell adhesion, migration, proliferation and death. avb6, one of these integrins, is constituted of av and b6 subunit responsible for activation of TGF-B1/B3. avb6 expression is strictly limited to epithelial cells. Under normal physiological conditions, avb6 expression is almost exclusively restricted to specific tissue morphological changes during developmental phases leading to low or no expression in fully differentiated epithelia with some exceptions. Under pathological tissue reprogramming, avb6 expression is upregulated in tumor cell migration, wound healing and inflammation. The level of avb6 expression, in general, correlates with poor overall survival.

SUMMARY

In one aspect, polypeptides are disclosed comprising the amino acid sequence selected from the group consisting of SEQ ID NOS:1-3, wherein the polypeptide binds to alpha(v) beta (6) integrin (avb6). In one embodiment, the amino acid residue at position 8 is R, the amino acid residue at position 9 is G, and the amino acid residue at position 10 is D. In various other embodiments, the amino acid residue at position 12 is A; the amino acid residue at position 13 is E or T; the amino acid residue at position 14 is L; the amino acid residue at position 15 is M, R or K; the amino acid residue at position 16 is L; the amino acid residue at position 37 is N, S, or K; the amino acid residue at position 38 is G; wherein the amino acid residue at position 39 is A, F, or K; the amino acid residue at position 40 is E; the amino acid residues at position 61 is R or K; the amino acid residues at position 62-67 are FP(G/R)(V/T)XT, where X is any residue recited at position 66 in Table 1, 2, or 3 and wherein residues in parentheses are alternatives at that position, the amino acid residue at position 17 is R; the amino acid residue at position 36 is N; and/or; the amino acid residue at position 65 is V, and/or the amino acid residue at position 67 is T.

In another embodiment, the polypeptides comprise an amino acid sequence at least 50%, 55%, 60%, 65%, 70%, 75%, 80%, 85%, 90%, 91%, 92%, 93%, 94%, 95%, 96%, 97%, 98% identical to the amino acid sequence of SEQ ID NOS:4-30. In one embodiment, residues 8-10 are invariant, and optionally wherein 1, 2, 3, 4, 5, 6, 7, 8, 9, 10, 11, 12, 13, 14, 15, 16, or all 17 of the amino acid residues at positions 12, 13, 14, 15, 16, 17, 36, 37, 38, 39, 40, 61, 62, 63, 64, 65, and 67 are invariant from the reference sequence, residue numbering starting from the first amino acid after the optional N-terminal methionine residue for SEQ ID NOS: 4-28, and starting from the third amino acid (Cys residue) after the optional N-terminal methionine residue for SEQ ID NOS:29-30.

In another aspect, the disclosure provides polypeptides at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:4-30 and 36. In one embodiment, the polypeptide is at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:21, 25, and 29-30.

In another embodiment, amino acid changes from the reference protein are conservative amino acid substitutions. In a further embodiment, the RGD sequence is invariant. In one embodiment, residues 8-10 are invariant, and optionally wherein 1, 2, 3, 4, 5, 6, 7, 8, 9, 10, 11, 12, 13, 14, 15, 16, or all 17 of the amino acid residues at positions 12, 13, 14, 15, 16, 17, 36, 37, 38, 39, 40, 61, 62, 63, 64, 65, and 67 are invariant from the reference sequence, residue numbering starting from the first amino acid after the optional N-terminal methionine residue for SEQ ID NOS: 4-28, and starting from the third amino acid (Cys residue) after the optional N-terminal methionine residue for SEQ ID NOS: 29-30 In other aspects, the disclosure provides nucleic acids encoding the polypeptide of any embodiment or combination of embodiments disclosed herein; expression vectors comprising the nucleic acid operatively linked to a control sequence; host cells or recombinant comprising the nucleic acid or the expression vector of any embodiment or combination of embodiments disclosed herein; and pharmaceutical composition comprising the polypeptide, nucleic acid, expression vector, host cell, or recombinant cell of any embodiment or combination of embodiments disclosed herein and a pharmaceutically acceptable carrier.

In one aspect, the disclosure provides uses of the polypeptide, nucleic acid, expression vector, host cell, recombinant cell, or pharmaceutical composition of any embodiment or combination of embodiments disclosed herein for any suitable purpose, including but not limited to treating and/or detecting avb6(+) tumors in vivo, blocking avb6 mediated TGF-B signaling in vitro, and treating pulmonary fibrosis such as Idiopathic Pulmonary Fibrosis (IPF). In another aspect, the disclosure provides methods for treating an avb6(+) tumor or pulmonary fibrosis such as Idiopathic Pulmonary Fibrosis (IPF), comprising administering to a subject in need thereof an amount of the polypeptide, nucleic acid, expression vector, host cell, and/or pharmaceutical composition of any embodiment or combination of embodiments disclosed herein effective to treat the tumor or IPF in the subject. In a further aspect, the disclosure provides methods for detecting an avb6(+) tumor, comprising administering to a subject suspected of having an avb6(+) tumor an amount of the polypeptide, nucleic acid, expression vector, host cell, and/or pharmaceutical composition of any embodiment or combination of embodiments disclosed herein effective to detect the tumor in the subject.

In another aspect, the disclosure provides methods for designing avb6-binding polypeptides, comprising the steps of any embodiment or combinations of embodiments disclosed herein and in the attached appendices.

DETAILED DESCRIPTION

Figure 1:
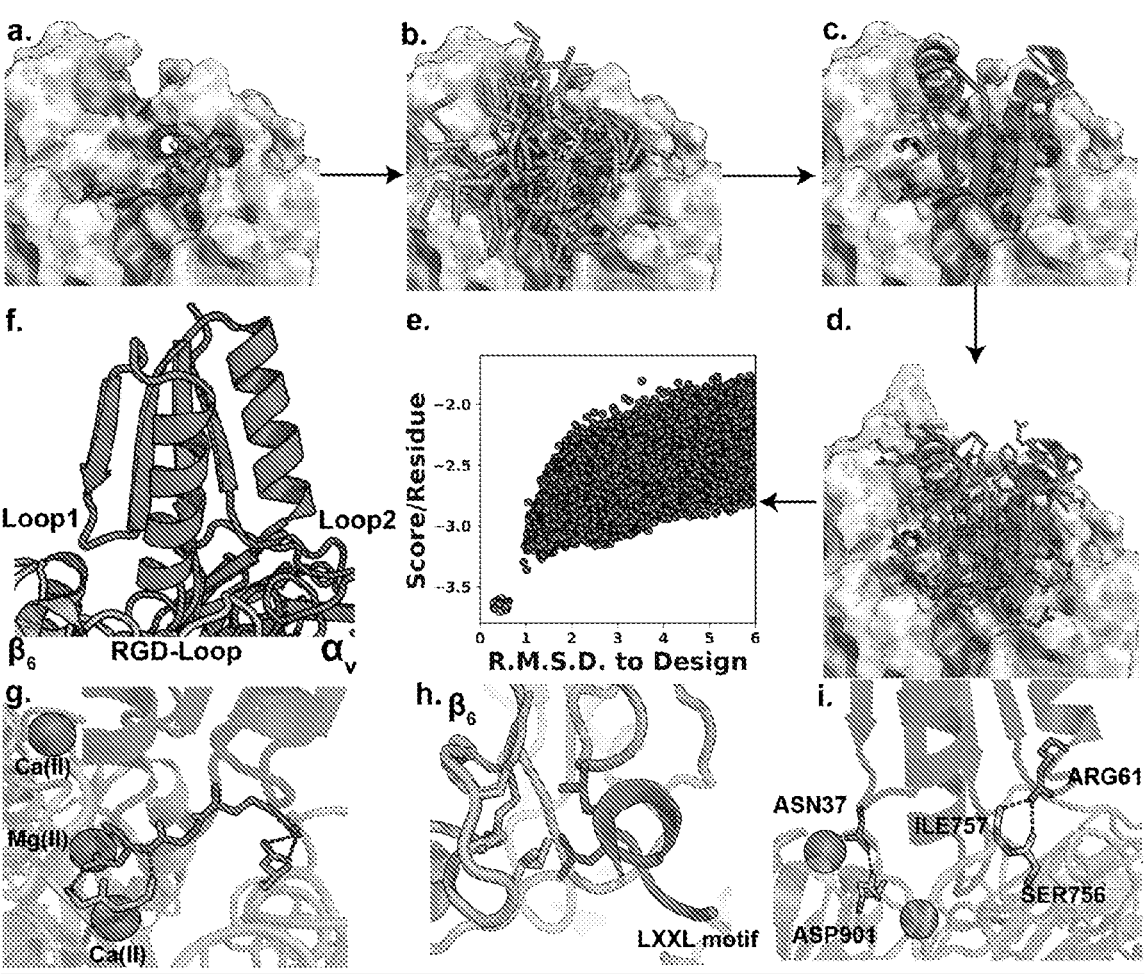
FIG. 1a-i. a) Computational design strategy for a $\alpha_v\beta_6$ binding protein: Structure of the $\alpha_v\beta_6$ integrin (surface representation) in complex with TGF-β1 peptide (cartoon representation, PDB ID 4UM9). b) Low RMSD matches to the TGF-β1 peptide were harvested from the PDB database (ribbon representation). c) Non-clashing fragments were then incorporated in the α/β ferredoxin folds (cartoon representation) using Rosetta™. d) Rosetta™ flexible sequence design was performed keeping the RGD binding loop fixed. e) Rosetta™ Structure prediction was then used to identify sequences for which the designed structure is the lowest energy state. f) In addition to the RGD binding motif, two loops (Loop1 and Loop2) mediate contact with $\alpha_v$ and $\beta_6$ subunit. g) Canonical RGD motif in design av6_3 makes backbone level interactions with the receptor and Asp coordinates to the Mg(II). h) The -LXXL (SEQ ID NO:33) motif immediately following the RGD binding loop packs against the hydrophobic groove on the $\beta_6$ subunit. i) Additional interactions mediated by loop1 and loop2 that make polar contacts with $\beta_6$ and $\alpha_v$ subunit, respectively.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, CA), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, CA), *Culture of Animal Cells: A Manual of Basic Technique, 2nd* Ed. (R. I. Freshney. 1987. Liss, Inc. New York, NY), *Gene Transfer and Expression Protocols*, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise.

As used herein, "about" means+/−5% of the recited value.

All embodiments of any aspect of the disclosure can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In one aspect, the disclosure provides polypeptide comprising the amino acid sequence of SEQ ID NO:1, 2, or 3 (as shown in Table 1, Table 2, or Table 3), wherein the Table shows amino acid options at each position in the polypeptide, and wherein the polypeptide binds to alpha(v) beta (6) integrin (avb6). As disclosed in the examples herein, the inventors have designed the claimed polypeptides as avb6 integrin binding proteins. The designed proteins are hyperthermostable and bind to avb6 with high affinity. The polypeptides can be used, for example, to treat and/or detect avb6(+) tumors in vivo, to block avb6 mediated TGF-B signaling in vitro, and to treat pulmonary fibrosis such as Idiopathic Pulmonary Fibrosis (IPF). The examples provide saturation studies to identify residues that can be present at each position in the polypeptides.

TABLE 1

SEQ ID NO: 1, showing by single AA letter code the amino acid residues that may be present at any position in the polypeptide, based on saturation mutagenesis studies described in the examples that follow.
Residue position 1: A, C, D, E, F, G, I, K, L, M, R, S, T, V, W, Y position 2: V, A, C, D, E, G, I, L, M, R, S, T, W, Y position 3: V, A, C, D, F, G, I, L, N, Q position 4: R, A, C, F, G, I, K, M, N, S, V position 5: F, A, C, E, G, H, I, K, L, M, N, P, R, V, W, Y position 6: V, A, D, G, H, I, K, L, M, N, Q, R, S, T position 7: F, A, C, D, G, H, I, K, L, R, S, T, V, Y position 8: R, E, G, I, K, S, T, V position 9: G, C, D, R, S position 10: D, A, E, H, V, Y position 11: L, F, M, Q, S position 12: A, E, G, K, P, R, S, T, V position 13: E, A, D, F, G, H, I, K, L, M, N, P, Q, R, S, T, V, W, Y position 14: L, E, F, K, M, R, S, V position 15: M, A, C, E, G, H, I, K, L, N, P, Q, R, S, T, V, W position 16: L, A, F, G, K, M, N, Q, R, S, T, V, W position 17: R, C, G, K, M, S, W position 18: A, E, F, G, H, I, S, T, V, W, Y position 19: V, A, C, D, E, F, G, I, L, P, S, T, W position 20: K, A, E, F, G, M, N, P, Q, R, S, T, Y position 21: D, A, C, E, F, G, H, I, K, L, M, N, P, Q, R, S, T, V, W, Y position 22: H, D, G, M, N, P, Q, R, V, W, Y position 23: L, C, E, F, G, M, Q, S, V, W position 24: K, C, G, M, N, Q, R, S, T, W position 25: K, E, F, M, N, P, Q, R, S, V position 26: E, C, D, G, K, N, Q, R, S, V, W position 27: G, A, C, D, E, L, N, R, S, V position 28: P, A, D, E, G, K, L, M, N, Q, R, T, V position 29: H, A, C, D, E, G, I, K, L, M, N, P, Q, R, S, T, V, Y position 30: W, C, D, G, I, L, R, S, T position 31: N, A, D, E, F, G, H, I, K, L, M, R, S, V, W, Y position 32: I, F, H, L, M, P, R, S, T, V, W position 33: T, A, C, E, F, G, H, I, K, L, M, N, P, Q, R, S, V, W, Y TABLE 1-continued SEQ ID NO: 1, showing by single AA letter code the amino acid
residues that may be present at any position in the polypeptide,
based on saturation mutagenesis studies described in the examples
that follow.
Residue position 34: S, A, D, G, K, L, M, N, P, Q, R, T, V, W position 35: T, A, F, G, I, K, L, N, P, Q, R, S, V, W, Y position 36: N, A, D, E, G, I, K, L, P, Q, R, S, T, V position 37: N, A, D, G, H, I, K, L, M, P, Q, R, S, T, V, W, Y position 38: G, A, D, E, H, I, K, L, M, P, Q, R, S, T, V, Y position 39: A, C, D, E, G, K, I, K, L, M, N, P, Q, R, S, T, V, W, Y position 40: E, A, C, D, G, H, K, M, N, P, Q, R, S, T, V, W, Y position 41: L, C, D, F, G, H, K, P, Q, R, S, V, W position 42: V, A, D, E, F, G, I, K, L, M, R, S, W, Y position 43: V, A, E, G, I, L, N, R, T position 44: R, A, E, G, I, K, L, M, Q, S, T, W position 45: G, A, C, D, E, K, L, M, N, Q, R, S, T, V, W, Y position 46: I, A, C, E, F, G, L, M, N, S, T, V position 47: H, A, D, E, F, G, I, K, L, M, N, P, Q, R, S, T, V, W, Y position 48: E, A, C, D, G, H, K, L, N, P, Q, R, S, T, V, W, Y position 49: S, A, D, E, F, G, H, I, K, L, N, P, R, T, V, W position 50: D, A, E, F, G, I, K, N, Q, R, S, T, V, W, Y position 51: A, E, G, R, S, T, V, Y position 52: K, A, C, D, E, F, G, H, I, L, M, N, Q, R, S, T, V, W position 53: R, A, C, D, E, G, H, I, L, M, N, Q, S, T, V, W position 54: I, F, M, N, T position 55: A, C, D, E, G, I, K, L, M, N, P, Q, R, S, T, V, W, Y position 56: K, A, D, E, F, G, I, L, M, N, P, R, S, T, V, W, Y position 57: W, A, C, F, G, H, I, L, M, Q, R, S, V, Y position 58: V, A, C, D, E, G, K, L, M, Q, R, S position 59: E, A, C, D, G, H, I, K, L, M, N, Q, R, S, T, V, Y position 60: K, E, F, I, M, N, R position 61: R, A, G, Q, S, W, K position 62: F, C, G, I, L, S, V, W, Y position 63: P, C, E, F, G, H, K, L, M, N, Q, R, S, T, W position 64: G, A, C, D, E, F, H, I, K, L, M, N, P, Q, R, S, T, V, W position 65: V, A, D, F, G, R, I, K, L, Q, R, 3, T position 66: K, A, C, D, F, G, K, L, N, Q, R, S, T, V, W, Y position 67: T, C, I, K, L, N, R, S, V, Y position 68: E, A, D, F, G, K, M, N, Q, R, S, T, W, Y position 69: T, A, G, I, K, L, M, P, R, S, V, W position 70: Q, E, H, I, M, R, S, V TABLE 1-continued

| SEQ ID NO: 1, showing by single AA letter code the amino acid residues that may be present at any position in the polypeptide, based on saturation mutagenesis studies described in the examples that follow. |
| --- |
| Residue |
| position 71: Q, C, D, E, G, H, K, L, P, R, S, T, V, W |
| position 72: D, A, C, E, G, L, N, Q, R, S, V, Y |

TABLE 2

| SEQ ID NO: 2, showing by single AA letter code the amino acid residues that may be present at any position in the polypeptide, including more enriched mutations seen in the saturation mutagenesis studies described in the examples that follow. |
| --- |
| position 1: A, C, E, K, T |
| position 2: V, L, M, R |
| position 3: V |
| position 4: R, S |
| position 5: F, G, K, L, M, R |
| position 6: V, A, K, R |
| position 7: F, A, G, K, R |
| position 8: R |
| position 9: G |
| position 10: D |
| position 11: L |
| position 12: A, G, K, R |
| position 13: E, A, F, G, H, 1, K, L, M, P, Q, R, S, T, V, W, Y |
| position 14: L, S |
| position 15: M, K,L,R,V |
| position 16: L, R |
| position 17: R |
| position 18: A, F, V |
| position 19: V, A, C, S |
| position 20: K, R |
| position 21: D, A, F, G, H, R, S, T, V, W, Y |
| position 22: H |
| position 23: L, V |
| position 24: K, G, R |
| position 25: K |
| position 26: E, R, W |
| position 27: G, L, S |
| position 28: P, K, M, V |
| position 29: H, G, L, N, R, S |

TABLE 2-continued

| SEQ ID NO: 2, showing by single AA letter code the amino acid residues that may be present at any position in the polypeptide, including more enriched mutations seen in the saturation mutagenesis studies described in the examples that follow. |
| --- |
| position 30: W |
| position 31: N, R, S, W |
| position 32: I, F, W |
| position 33: T, F, G, R, S, V, W, Y |
| position 34: S, G, K, R |
| position 35: T, A, G, I, P, S |
| position 36: N, A, G, R, V |
| position 37: N, A, G, L, R, S, T, V, W |
| position 38: A, K, R, S |
| position 39: A, G, H, K, L, N, P, R, S, T, V |
| position 40: E, A, G, Q, R, S, T |
| position 41: L |
| position 42: V, F |
| position 43: V |
| position 44: R, K |
| position 45: G, R, S |
| position 46: I, V |
| position 47: H, G, P, R, V |
| position 48: E, A, G, H, K, L, R |
| position 49: S, D, F, I, R, W |
| position 50: D, E, G, S |
| position 51: A |
| position 52: K, D, F, N, Q, R, S, T, V |
| position 53: R, A, D, M, Q, V |
| position 54: I |
| position 55: A, E, G, S, T |
| position 56: K, A, G, N, R |
| position 57: W, G, Y |
| position 58: V, K |

TABLE 2-continued

SEQ ID NO: 2, showing by single AA letter code
the amino acid residues that may be present at
any position in the polypeptide, including more
enriched mutations seen in the saturation
mutagenesis studies described in the examples
that follow.

position 59: E, A, G, K, L, Q, R, S, T, V position 60: K, I, M, N position 61: R position 62: F, W position 63: P, F, G, K, L, R, S position 64: G, Q, R, S, T, V position 65: V, T position 66: H, G, Q, R position 67: T position 68: E, R position 69: T position 70: Q, R position 71: Q, T, V position 72: D

TABLE 3

SEQ ID NO: 3, showing by single AA letter code
the amino acid residues that may be present at
any position in the polypeptide, including even
more enriched mutations seen in the saturation
mutagenesis studies described in the examples
that follow.

position 1: A, K, C position 2: V, L, R position 3: V position 4: R position 5: F, G, M, R position 6: V, R position 7: F, G, R position 8: R position 9: G position 10: D position 11: L position 12: A, G, K position 13: E, A, F, G, H, I, L, P, R, S, T, V, W, Y position 14: L, S position 15: M, K,R,V position 16: L TABLE 3-continued SEQ ID NO: 3, showing by single AA letter code
the amino acid residues that may be present at
any position in the polypeptide, including even
more enriched mutations seen in the saturation
mutagenesis studies described in the examples
that follow.

position •17: R position 18: A, V position 19: V, A, S position 20: K position 21: D, A, F, G, R, S, W position 22: H position 23: L, V position 24: K, G, R position 25: K position 26: E, R position 27: G position 28: P, K, V position 29: H position 30: W position 31: N, R, S position 32: I, W position 33: T, G, R, V position 34: S, G, K, R position 35: T, A, G position 36: N, G, R, V position 37: N, G, R, T, V, W position 38: A, K, R, S position 39: A, G, H, K, P, R, S, V position 40: E, G, R, S position 41: L position 42: V position 43: V position 44: R position 45: G, R position 46: I position 47: H, R, V position 48: E, H, L position 49: S, F, I, R position 50: D, E position 51: A position 52: K, N, S TABLE 3-continued SEQ ID NO: 3, showing by single AA letter code
the amino acid residues that may be present at
any position in the polypeptide, including even
more enriched mutations seen in the saturation
mutagenesis studies described in the examples
that follow.

```
position 53: R, A, D, Q position 54: I position 55: A, E, G, S, T position 56: K, A, G, N, R position 57: W, Y position 58: V position 59: E, A, G, K, L, R, T, V position 60: K, I position 61: R position 62: F, W position 63: P, G, K, R, S position 64: G, Q, R, S, T, V position 65: V position 66: H, G, Q, R position 67: T position 68: E, R position 69: T position 70: Q position 71: Q, T, V position 72: D
```

In one embodiment, the amino acid residue at position 8 is R, the amino acid residue at position 9 is G, and the amino acid residue at position 10 is D. Interface residues for avb6 binding include position 8-10, and in this embodiment the interface residues comprise an RGD motif at residues 8-10.

In various further embodiments that may be combined:
the amino acid residue at position 12 is A;
the amino acid residue at position 13 is E or T;
the amino acid residue at position 14 is L;
the amino acid residue at position 15 is M, R or K;
the amino acid residue at position 16 is L;
the amino acid residue at position 17 is R;
the amino acid residue at position 36 is N;
the amino acid residue at position 37 is N, S, or K;
the amino acid residue at position 38 is G;
the amino acid residue at position 39 is A, F, or K;
the amino acid residue at position 40 is E;
the amino acid residues at position 61 is R or K;
the amino acid residues at position 62-67 are FP(G/R)(V/ T)XT (SEQ ID NO:35), where X is any residue recited at position 66 in Table 1, 2, or 3 and wherein residues in parentheses are alternatives at that position;
the amino acid residue at position 65 is V; and/or
the amino acid residue at position 67 is T.
In other embodiments that may be combined:
the amino acid residue at position 12 is A;
the amino acid residue at position 13 is E or T;
the amino acid residue at position 14 is L;
the amino acid residue at position 15 is M, R or K;
the amino acid residue at position 17 is R;
the amino acid residue at position 36 is N;
the amino acid residue at position 37 is N, S, or K;
the amino acid residue at position 38 is G;
the amino acid residue at position 39 is A, F, or K;
the amino acid residues at position 61 is R or K;
the amino acid residues at position 62-67 are FP(G/R)(V/ T)XT (SEQ ID NO:35), where X is any residue recited at position 66 in Table 1, 2, or 3 and wherein residues in parentheses are alternatives at that position;
the amino acid residue at position 65 is V; and/or
the amino acid residue at position 67 is T.
As described in the examples that follow, the amino acid residue at positions 12-17, 36-40, 61-65, and 67 of the polypeptide may directly contact avb6.
In another embodiment, the polypeptide comprises an amino acid sequence at least 50%, 55%, 60%, 65%, 70%, 75%, 80%, 85%, 90%, 91%, 92%, 93%, 94%, 95%, 96%, 97%, 98% identical to the amino acid sequence of SEQ ID NOS:4-28, wherein residues in parentheses are optional. Each of these embodiments includes an optional N-terminal methionine that is not included in SEQ ID NOS:1-3. Thus, the residue numbering in SEQ ID NOS:4-28 begins with the first amino acid after the optional N-terminal methionine residue.

TABLE 4

| av6_1 | (M)AVVRFVFRGDLAELMLRAVKDHLKKEGPHWNITSTNNGAELVVRGIHESDAKRIART VEKLTNGKSQSLVLT (SEQ ID NO: 4) |
| --- | --- |
| av6_2 | (M)AVVRFVFRGDLAELMLRAVKDHLKKEGPHWNITSTNNGAELVVRGIHESDAKRIANW AKTYSPGGKESYTIP (SEQ ID NO: 5) |
| av6_3 | (M)AVVRFVFRGDLAELMLRAVKDHLKKEGPHWNITSTNNGAELVVRGIHESDAKRIAKW VEKRFPGVHTETQQD (SEQ ID NO: 6) |
| av6_4 | (M)AVVRFVFRGDLAELMLRAVKDHLKKEGPHWNITSTNNGAELVVRGIHESDAKRIAKW ARLKFPGTDTRIEVR (SEQ ID NO: 7) |
| av6_5 | (M)AVVRFVFRGDLAELMLRAVKDHLKKEGPHWNITSDESGFELVVRGIHESDAKRIART VEKLTNGKSQSLVLT (SEQ ID NO: 8) |
| av6_6 | (M)AVVRFVFRGDLAELMLRAVKDHLKKEGPHWNITSDESGFELVVRGIHESDAKRIANW AKTYSPGGKESYTIP (SEQ ID NO: 9) |
| av6_7 | (M)AVVRFVFRGDLAELMLRAVKDHLKKEGPHWNITSDESGFELVVRGIHESDAKRIAKW VEKRFPGVHTETQQD (SEQ ID NO: 10) |

TABLE 4-continued

```
av6_8      (M)AVVRFVFRGDLAELMLRAVKDHLKKEGPHWNITSDESGFELVVRGIHESDAKRIAKW
           ARLKFPGTDTRIEVR (SEQ ID NO: 11)

av6_9      (M)AVVRFVFRGDLAELMLRAVKDHLKKEGPHWNITSDTSKGAELVVRGIHESDAKRIAR
           TVEKLTNGKSQSLVL (SEQ ID NO: 12)

av6_10     (M)AVVRFVFRGDLAELMLRAVKDHLKKEGPHWNITSDTSKGAELVVRGIHESDAKRIAN
           WAKTYSPGGKESYTI (SEQ ID NO: 13)

av6_11     (M)AVVRFVFRGDLAELMLRAVKDHLKKEGPHWNITSDTSKGAELVVRGIHESDAKRIAK
           WVEKRFPGVHTETQQ (SEQ ID NO: 14)

av6_12     (M)AVVRFVFRGDLAELMLRAVKDHLKKEGPHWNITSDTSKGAELVVRGIHESDAKRIAK
           WARLKFPGTDTRIEV (SEQ ID NO: 15)

av6_13     (M)AWRFVFRGDLAELMLRAVKDHLKKEGPHWNITSVESSQVELVVRGIHESDAKRIAR
           TVEKLTNGKSQSLVL (SEQ ID NO: 16)

av6_14     (M)AVVRFVFRGDLAELMLRAVKDHLKKEGPHWNITSVESSQVELVVRGIHESDAKRIAN
           WAKTYSPGGKESYTI (SEQ ID NO: 17)

av6_15     (M) AWRFVFRGDLAELMLRAVKDHLKKEGPHWNITSVESSQVELVVRGIHESDAKRIAK
           WVEKRFPGVHTETQQ (SEQ ID NO: 18)

av6_16     (M) AWRFVFRGDLAELMLRAVKDHLKKEGPHWNITSVESSQVELVVRGIHESDAKRIAK
           WARLKFPGTDTRIEV (SEQ ID NO: 19)

M15R       (M)AVVRFVFRGDLAELRLRAVKDHLKKEGPHWNITSTNNGAELVVRGIHESDAKRIAKW
           VEKRFPGVHTETQQD (SEQ ID NO: 20)

E13T       (M)AVVRFVFRGDLATLMLRAVKDHLKKEGPHWNITSTNNGAELVVRGIHESDAKRIAKW
(BPI)      VEKRFPGVHTETQQD (SEQ ID NO: 21)

A39K       (M)AVVRFVFRGDLAELMLRAVKDHLKKEGPHWNITSTNNGKELVVRGIHESDAKRIAKW
           VEKRFPGVHTETQQD (SEQ ID NO: 22)

G64R       (M)AVVRFVFRGDLAELMLRAVKDHLKKEGPHWNITSTNNGAELVVRGIHESDAKRIAKW
           VEKRFPRVHTETQQD (SEQ ID NO: 23)

M15RG64R   (M)AVVRFVFRGDLAELRLRAVKDHLKKEGPHWNITSTNNGAELVVRGIHESDAKRIAKW
           VEKRFPRVHTETQQD (SEQ ID NO: 24)

A39KG64R   (M)AVVRFVFRGDLAELMLRAVKDHLKKEGPHWNITSTNNGKELVVRGIHESDAKRIAKW
(BP2)      VEKRFPRVHTETQQD (SEQ ID NO: 25)

E13TG64R   (M)AVVRFVFRGDLATLMLRAVKDHLKKEGPHWNITSTNNGAELVVRGIHESDAKRIAKW
           VEKRFPRVHTETQQD (SEQ ID NO: 26)

E13TM15    (M)AVVRFVFRGDLATLRLRAVKDHLKKEGPHWNITSTNNGKELVVRGIHESDAKRIAKW
RA39K      VEKRFPGVHTETQQD (SEQ ID NO: 27)

E13TM15    (M)AVVRFVFRGDLATLRLRAVKDHLKKEGPHWNITSTNNGKELVVRGIHESDAKRIAKW
RA39KG6    VEKRFPRVHTETQQD (SEQ ID NO: 28)
4R

AEVRFVFRGDLTELMLRAVKDHLKKEGPHWNITSRGNELEVRGSHESDAKRIQKEFPSVOSTTQA
                        (SEQ ID NO: 36)
```

In other embodiments, the polypeptide comprises an amino acid sequence at least 500% 55% %, 60%, 65% %, 70%, 75%, 80%, 85% %, 90%, 91%, 92% %, 93% %, 94%, 95% %, 96%, 97%, 98% identical to the amino acid sequence of SEQ ID NOS:29-30, wherein residues in parentheses are optional. Each of these embodiments includes an optional N-terminal methionine and two additional residues at the N-terminus that are not included in SEQ ID NOS: 1-3.

Thus, the residue numbering in SEQ ID NOS:29-30 begins with the third amino acid (Cys residue) after the optional N-terminal methionine residue. These embodiments have introduced Cys residues that permit disulfide bonding. Introduction of a disulfide bond made both proteins hyper-thermostable, maintaining their secondary structure at 95° C. suggested by CD spectroscopy data under non-reducing conditions

```
BP1 (E13       (M)TKCVVRFVFRGDLATLMLRAVKDHLKKEGPHWNITSTNNCAELVVRGIHESDAKRIA
T_disulf2)     KWVEKRFPGVHTETQCD (SEQ IE NO: 29)

BP2(A39        (M)TKCVVRFVFRGDLAELMLRAVKDHLKKEGPHWNITSTNNGKELVVRGIHESDAKRIA
KG64R_         KWVEKRFPRVHTETQCD (SEQ ID NO: 30)
disulf2)
```

In one embodiment the polypeptide is at least 50%, 55%, 60%, 65%, 70%, 75%, 80%, 85%, 90%, 91%, 92%, 93%, 94%, 95%, 96%, 97%, 98%, 99%, or 1000% identical to the amino acid sequence selected from the group consisting of SEQ ID NOS: 21 (ET3T) and SEQ ID NO:25 (A39KG64R).

In one embodiment, residues 8-10 (residue numbering starting from the first amino acid after the optional N-terminal methionine residue) are invariant. As noted above, interface residues for avb6 binding include position 8-10 In another embodiment, 1, 2, 3, 4, 5, 6, 7, 8, 9, 10, 11, 12, 13, 14, 15, 16, or all 17 of the amino acid residues at positions 12, 13, 14, 15, 16, 17, 36 37, 38, 39, 40, 61, 62, 63, 64, 65, and 67 (residue numbering starting from the first amino acid after the optional N-terminal methionine residue for SEQ ID NOS: 4-28, and starting from the third amino acid (Cys residue) after the optional N-terminal methionine residue for SEQ ID NOS:29-30) are invariant from the reference sequence. As noted above, the amino acid residue at position 12-17, 36-40, 61-65, and 67 of the polypeptide may directly contact avb6.

In another aspect, the disclosure provides polypeptides that is are least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:4-30 and 36.

```
                                        (SEQ ID NO: 36)
AEVREVFRGDLTELMLRAVKDHLKKEGPHWNITSRGNELEVRGSHESDAK

RIQKEFPSVQSTTQA
```

In one embodiment the polypeptides of this aspect are at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS: 21 (E13T), 25 (A39KG64R), and 29-30.

In one embodiment, residues 8-10 (residue numbering starting from the first amino acid after the optional N-terminal methionine residue) of SEQ ID NOS:4-30, or residues 10-12 of SEQ ID NOS:29-30 are invariant. As noted above, interface residues for avb6 binding include position 8-10 (or 10-12 in SEQ ID NOS:29-30). In another embodiment, 1, 2, 3, 4, 5, 6, 7, 8, 9, 10, 11, 12, 13, 14, 15, 16, or all 17 of the amino acid residues at positions 12, 13, 14, 15, 16, 17, 36, 37, 38, 39, 40, 61, 62, 63, 64, 65, and 67 are invariant from the reference sequence, residue numbering starting from the first amino acid after the optional N-terminal methionine residue for SEQ ID NOS: 4-28, and starting from the third amino acid (Cys residue) after the optional N-terminal methionine residue for SEQ ID NOS:29-30. As noted above, the amino acid residue at position 12-17, 36-40, 61-65, and 67 of the polypeptide may directly contact avb6.

In one embodiment all of the above embodiments, amino acid changes from the reference protein may be conservative amino acid substitutions.

As used here, "conservative amino acid substitution" means that:

hydrophobic amino acids (Ala, Cys, Gly, Pro, Met, Sce, Sme, Val, Ile, Leu) can only be substituted with other hydrophobic amino acids;

hydrophobic amino acids with bulky side chains (Phe, Tyr, Trp) can only be substituted with other hydrophobic amino acids with bulky side chains;

amino acids with positively charged side chains (Arg, His, Lys) can only be substituted with other amino acids with positively charged side chains;

amino acids with negatively charged side chains (Asp, Glu) can only be substituted with other amino acids with negatively charged side chains; and amino acids with polar uncharged side chains (Ser, Thr, Asn, Gln) can only be substituted with other amino acids with polar uncharged side chains.

In one embodiment, the polypeptide of the disclosure may be linked to a detectable label. This embodiment may be useful, for example, in diagnostic uses of the polypeptides. Any suitable detectable label may be used as deemed appropriate for an intended use, including but not limited to radioactive labels, fluorescent or luminescent proteins, avidin, biotin, or enzymes such as peroxidase.

In all embodiments, the polypeptide binds to alpha(v) beta (6) integrin (avb6) as demonstrated by biolayer interferometry with his-tagged Ni-NTA sensors, as detailed in the examples that follow. In one embodiment, the polypeptide binds to avb6 with sub-nanomolar binding affinity using biolayer interferometry with his-tagged Ni-NTA sensors, as detailed in the examples that follow (Table 5). In another embodiment, the polypeptide binds to avb6 with at least 100-fold selectivity compared to alpha(v) beta (8) integrin (avb8), alpha(v) beta (1) integrin (avb1), alpha(v) beta (3) integrin (avb3), alpha(v) beta (5) integrin (avb5), alpha 5 beta 1 (a5b1), alpha 8 beta 1 (a8b1), and alpha (iib) beta (3) integrin (aiibb3) using K562 cells stably transfected with corresponding integrins.

In another aspect the disclosure provides nucleic acids encoding the polypeptide of any embodiment or combination of embodiments of the disclosure. The nucleic acid sequence may comprise single stranded or double stranded RNA or DNA in genomic or cDNA form, or DNA-RNA hybrids, each of which may include chemically or biochemically modified, non-natural, or derivatized nucleotide bases. Such nucleic acid sequences may comprise additional sequences useful for promoting expression and/or purification of the encoded polypeptide, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the disclosure.

In a further aspect, the disclosure provides expression vectors comprising the nucleic acid of any aspect of the disclosure operatively linked to a suitable control sequence. "Expression vector" includes vectors that operatively link a nucleic acid coding region or gene to any control sequences capable of effecting expression of the gene product. "Control sequences" operably linked to the nucleic acid sequences of the disclosure are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In various embodiments, the expression vector may comprise a plasmid, viral-based vector, or any other suitable expression vector.

In another aspect, the disclosure provides host cells or recombinant cells that comprise the nucleic acids, expression vectors (i.e.: episomal or chromosomally integrated), and/or polypeptides disclosed herein, wherein the host cells can be either prokaryotic or eukaryotic. The cells can be transiently or stably engineered to incorporate the expression vector of the disclosure, using techniques including but not limited to bacterial transformations, calcium phosphate co-precipitation, electroporation, or liposome mediated-, DEAE dextran mediated-, polycationic mediated-, or viral mediated transfection.

In another aspect, the disclosure provides pharmaceutical composition comprising:

(a) the polypeptide, the nucleic acid, the expression vector, or host cell of any embodiment or combination of embodiments disclosed herein; and (b) a pharmaceutically acceptable carrier.

The pharmaceutical compositions of the disclosure can be used, for example, in the methods of the disclosure described herein. The pharmaceutical composition may comprise in addition to the polypeptide of the disclosure (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides, nucleic acids, expression vectors, and/or host cells may be the sole active agent in the pharmaceutical composition, or the composition may further comprise one or more other active agents suitable for an intended use.

In another aspect, the disclosure provides use of the polypeptides, nucleic acids, expression vectors, host cells, or pharmaceutical composition of any embodiment or combination of embodiments disclosed herein for any suitable purpose, including but not limited to treating and/or detecting avb6(+) tumors in vivo, blocking avb6 mediated TGF-B signaling in vitro, and treating pulmonary fibrosis such as Idiopathic Pulmonary Fibrosis (IPF).

In another aspect, the disclosure provides methods for treating an avb6(+) tumor or pulmonary fibrosis such as Idiopathic Pulmonary Fibrosis (IPF), comprising administering to a subject in need thereof an amount of the polypeptide, nucleic acid, expression vector, host cell, and/or pharmaceutical composition of any embodiment or combination of embodiments disclosed herein effective to treat the tumor or IPF in the subject.

As detailed in the examples, high levels of $\alpha_v\beta_6$ expression are associated with poor overall survival in a wide range of cancers including non-small cell lung cancer (NSCLC) and pancreatic cancer. $\alpha_v\beta_6$ mediated activation of TGF-$\beta$ is also responsible for a wide variety of fibrotic diseases and an established target for therapeutic intervention in Idiopathic Pulmonary Fibrosis (IPF). IPF is a rare (10-60 cases per 100,000 people), progressive fibrotic lung disease of unknown cause for which there is no cure and accounts for 57% of all lung transplants. Patients suffering from acute respiratory distress syndrome (ARDS) resulting from ongoing and worsening COV-19 outbreak show patchy ground glass opacities on the lung tissue and are likely to develop lung fibrosis specifically in high risk older populations. SARS-CoV-2 infection recently has been shown to increase TGF-$\beta$ mRNA in lung and lung tissues along with other drivers of lung fibrosis following severe lung damage. Thus, in one embodiment the subject is a human subject that has IPF and is infected with SARS-CoV-2.

The subject may be any suitable subject, including but not limited to human subjects. As used herein, "treating" means accomplishing one or more of the following: (a) reducing the severity of the disorder; (b) limiting or preventing development of symptoms characteristic of the disorder; (c) inhibiting worsening of symptoms characteristic of the disorder; (d) limiting or preventing recurrence of the disorder in subjects that have previously had the disorder; and/or (e) limiting or preventing recurrence of symptoms in subjects that were previously symptomatic for the disorder. Any amount of such "treating" is of great benefit to a subject having an avb6(+) tumor or pulmonary fibrosis.

The short serum half-life (<2 hours), high specificity and affinity for $\alpha_v\beta_6$ target binding, ease of production using *E. coli*, hyper-thermostability, and aerosol formulatability of the polypeptides as described in the examples that follow provide significant improvements over existing therapeutics. In contrast to antibody inhibitors, the polypeptides of the disclosure can be formulated for tissue specific delivery with built-in tunable serum half-life and reduced systemic exposure, both factors which are expected to improve safety and reduce the chance of unwanted side effects (e.g. the lung residence and short serum half-life of an aerosol $\alpha_v\beta_6$ binder therapy for IPF could support better outcomes in eventual lung transplant settings for IPF patients).

The methods may comprise administration by any suitable route as deemed appropriate by attending medical personnel, including but not limited to pulmonary delivery (including but not limited to inhalation and nebulization), intravenous delivery, and intramuscular delivery.

In another aspect, the disclosure provides methods for detecting an avb6(+) tumor, comprising administering to a subject suspected of having an avb6(+) tumor an amount of the polypeptide, nucleic acid, expression vector, host cell, and/or pharmaceutical composition of any embodiment or combination of embodiments disclosed herein effective to detect the tumor in the subject.

In all embodiments, the subject may be any suitable subject, including but not limited to mammals such as humans.

In another aspect, the disclosure provides method for designing avb6-binding polypeptides, comprising the steps of any embodiment or combinations of embodiments disclosed herein. Details are provided in the examples that follow.

EXAMPLES

The integrin $\alpha_v\beta_6$ is an important therapeutic target linked to the activation of TGF-β1/β3 and is upregulated in a wide variety of cancers and a major driver of fibrotic diseases including Idiopathic Pulmonary Fibrosis (IPF) which can be triggered by coronavirus induced acute respiratory distress syndrome (ARDS). However, few highly specific avb6 inhibitors have been developed. We describe the de novo design of hyperstable inhibitory proteins that bind to human $\alpha_v\beta_6$ with sub-nanomolar affinity and with >2000× specificity over other RGD (Arg-Gly-Asp)-binding integrins. The crystal structure of the inhibitor closely matches the designed model with affinity and specificity stemming not only from an RGD containing loop but also a second loop that makes contacts with the β6 subunit. The designed inhibitor blocks $\alpha_v\beta_6$-mediated TGF-β signaling in vitro and enables specific targeting of $\alpha_v\beta_6$(+) tumors in vivo. The designed inhibitor shows considerable therapeutic efficacy against bleomycin induced IPF in mice when administered via intraperitoneal injection and shows promising preliminary efficacy as an inhaled therapeutic. Taken together, these results illustrate the power of de novo protein design in creating highly specific integrin inhibitors with therapeutic potential for immuno-oncology and the treatment of pulmonary fibrosis.

Introduction $\alpha_v\beta_6$ expression is upregulated upon tissue reprogramming during tumor cell migration, wound healing, and inflammation. High levels of $\alpha_v\beta_6$ expression are associated with poor overall survival in a wide range of cancers including non-small cell lung cancer (NSCLC) and pancreatic cancer. $\alpha_v\beta_6$ mediated activation of TGF-β is also responsible for a wide variety of fibrotic diseases and an established target for therapeutic intervention in Idiopathic Pulmonary Fibrosis (IPF). IPF is a rare (10-60 cases per 100,000 people), progressive fibrotic lung disease of unknown cause for which there is no cure and accounts for 57% of all lung transplants. Patients suffering from acute respiratory distress syndrome (ARDS) resulting from ongoing and worsening COV-19 outbreak show patchy ground glass opacities on the lung tissue and are likely to develop lung fibrosis specifically in high risk older populations. SARS-CoV-2 infection recently has been shown to increase TGF-β mRNA in lung and lung tissues along with other drivers of lung fibrosis following severe lung damage.

Based on the crystal structure of $\alpha_v\beta_6$ in complex with an RGD-containing peptide (pdb ID 4UM9), and as in other structures of RGD-containing peptides bound to integrins, the arginine and aspartate side chains make multiple hydrogen bonds to residues at the interface between the integrin alpha and beta subunits. C-terminal to the RGD, the peptide has an alpha-helical turn with two leucines fitting into a hydrophobic pocket formed by a 36 subunit loop. We sought to incorporate the RGD-containing peptide from the $\alpha_v\beta_6$ complex structure into a de novo designed protein with properties desirable in a therapeutic candidate. We began by screening candidate topologies in silico for hosting the 8 residue extended turn conformation of the peptide (RGDL-GALA (SEQ ID NO:31, FIG. 1a). We searched the PDB database for low RMSD matches to the peptide backbone conformation, and extracted segments consisting of the matched peptide plus the five flanking residues on both the N- and C-termini. These extended fragments were then superimposed on the bound peptide conformation in the complex structure, and those making backbone level clashes with the integrin were discarded (Figure Tb).

We found that small α/β ferredoxin structures (FIGS. 1c, 1d) were able to scaffold the binding loop without clashing with the integrin, and chose this fold for subsequent de novo design calculations. A two-step protocol was used to design $\alpha_v\beta_6$ binders with ferredoxin fold: In the first step, structures were assembled from fragments following rules for constructing ideal proteins, sampling different alpha helix, beta sheet and loop lengths, while constraining torsion angles in the region corresponding to the RGD peptide to those observed in the co-crystal structure using Rosetta™ (FIG. 1c). In the second step, the resulting idealized ferredoxin fold structures were docked in complex with the $\alpha_v\beta_6$ integrin by superposition on the binding loop, and the amino acids at the binding surface were optimized for low energy interactions with the target. The binding RGD motif was kept fixed during these design calculations (FIG. 1d). The final design models were subjected to ab initio structure prediction tests to identify those sequences for which the designed structure is the lowest energy state (FIG. 1e). Unlike most previous de novo designed protein-protein interfaces, all of the designed interactions between $\alpha_v\beta_6$ and the designed mini protein are mediated via loops (FIG. 1f). In addition to the RGD loop, there are two other loops that make contacts with $\alpha_v$ and $\beta_6$ subunit: Loop1 connecting sheet2 and sheet3 makes contact with $\beta_6$ subunit and loop2 connecting helix2 and sheet4 makes contact with $\alpha_v$ subunit (FIG. 1f).

Figure 4:
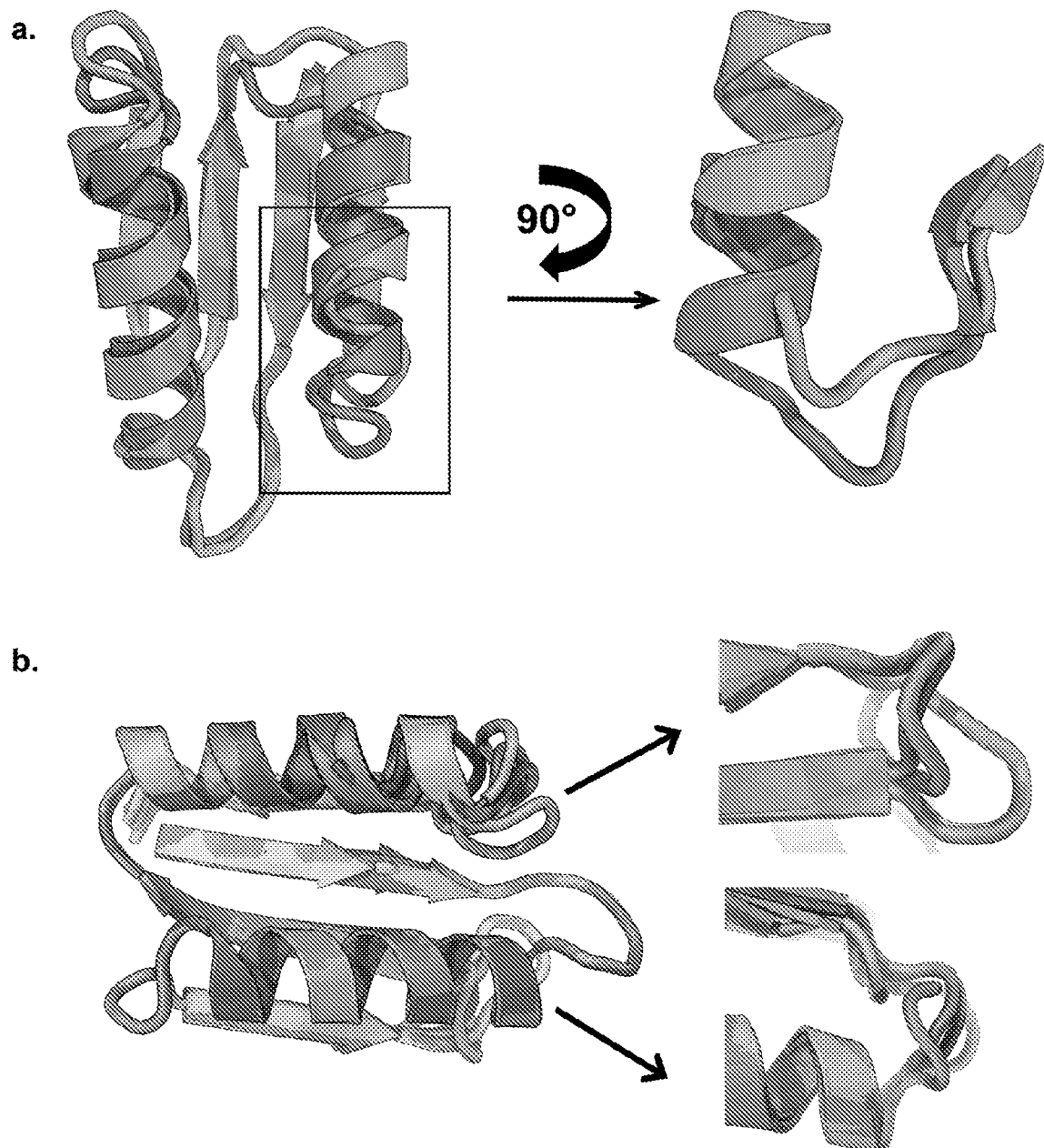
FIG. 4a-b. Crystal structure from the first round of design and second round design strategy: a) Crystal structure of the evolved variant (SEQ ID NO:36) from the first round of design superimposed onto the design model. Although the first part of the crystal structure including the RGD loop, overlaid well with the design model, there is a half-turn rotation of the last helix of the fold. b) For the second generation of designs, the crystal structure of the previous round was superimposed onto $\alpha_v\beta_6$ by aligning the RGD motif. Two loops were sampled for length and conformation and total 16 designs were ordered in the second round.

We obtained synthetic genes encoding 9 designs with different length helices, strands and loops (details of combinations in supplementary material). In initial testing by expression of candidate binders on the yeast cell surface, 4 designs bound to fluorescently labeled $\alpha_v\beta_6$ (biotinylated variant labeled with Streptavidin, R-Phycoerythrin Conjugate; SAPE) in a metal cation dependent manner as expected. Using the strongest binder, design 2, as a starting template, we constructed and screened error prone PCR and obtained a new variant with 5 mutations (02_E2V_T12A_E40V_S44I_T63I) after three rounds of yeast surface display and fluorescence activated cell sorting (FACS). We solved the crystal structure of this variant (SEQ ID NO:36) at 2A resolution. While the part of the crystal structure including the RGD loop overlaid very well with the computationally designed model, there is a half-turn rotation of the last helix of the fold. This is likely driven by the partially exposed Phe56 in the initial design model (FIG. 4).

Figure 5:
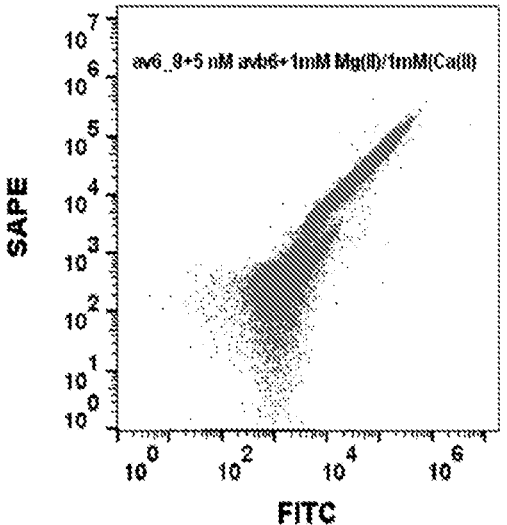
FIG. 5. Representative metal dependent binding of the designed proteins: The designed protein shows metal dependent binding to $\alpha_v\beta_6$. In the absence of any metal, there is no detectable binding (left panel) as compared to in presence of 1 mM Ca(II)/1 mM Mg(II) (right panel). Expression or FITC fluorescence is plotted (X-axis) against binding or SAPE fluorescence (Y-axis).
Figure 5:
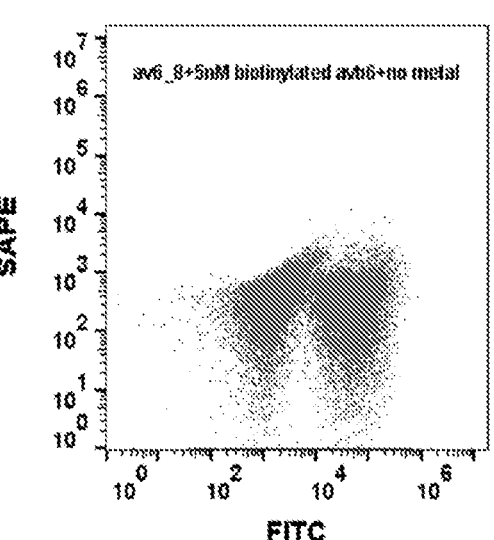
Figure 6:
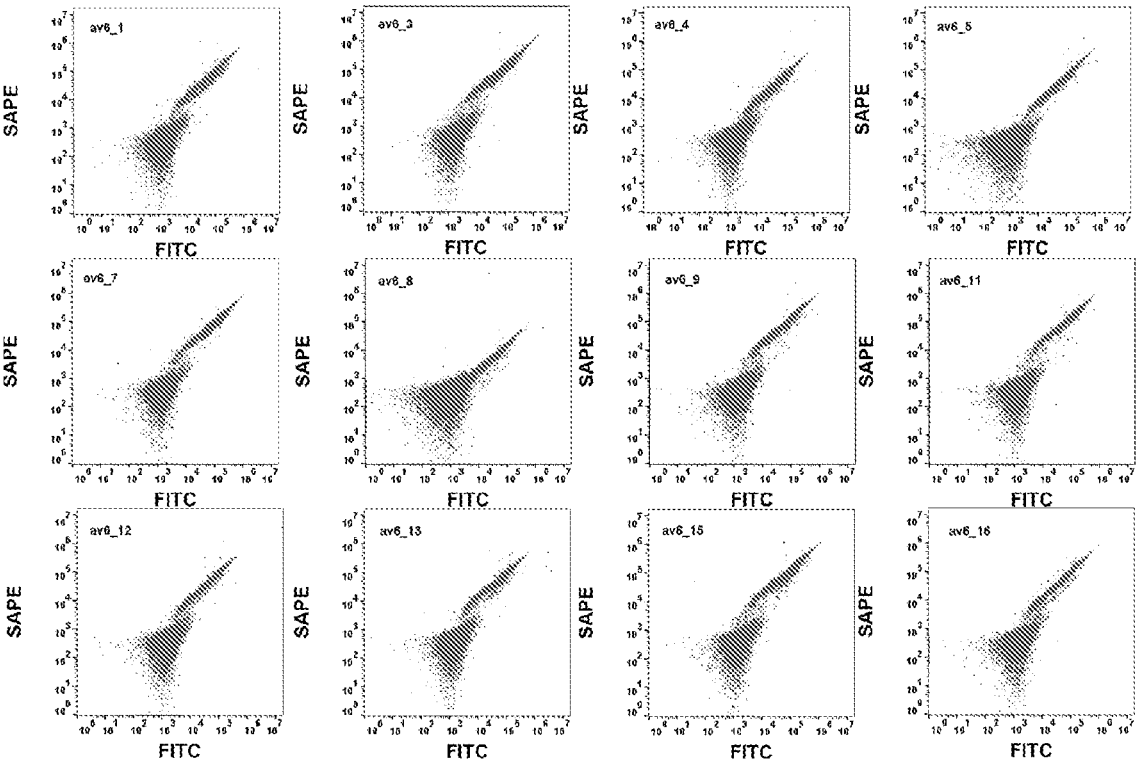
FIG. 6. Binding of 12 clones from second round of design on yeast surface using 50 pM biotinylated $\alpha_v\beta_6$. Expression or FITC fluorescence is plotted on X-axis and Binding or SAPE fluorescence is plotted on Y-axis.
Figure 7:
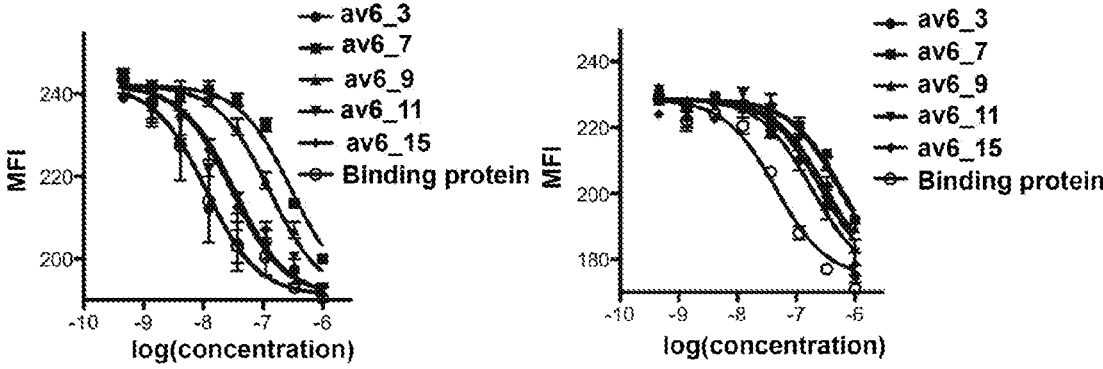
FIG. 7. In vitro cell surface competition assay of 5 strongest binders from the second round of designs. av6_3 shows the highest level of selectivity towards human $\alpha_v\beta_6$ as compared to human $\alpha_v\beta_8$. Log concentration of binder (X-axis) is plotted against Mean Fluorescence intensity (Y-Axis).

To generate $\alpha_v\beta_6$ binders with more extensive contacts with the integrin, in a second round of design, we docked the crystal structure of the designed binder from first round onto $\alpha_v\beta_6$ by superimposing on the RGD loop, and identified two loop regions in the design close to the integrin. We sampled a range of lengths and conformations for the two loops, and selected 16 designs with loops predicted to make specific interactions with the integrin for experimental testing. We obtained synthetic genes encoding these 16 designs, and measured binding using yeast surface display with bioti-nylated $\alpha_v\beta_6$ protein labeled with SAPE. Of the 16 ordered designs, 12 expressed well on the yeast surface and were found to bind $\alpha_v\beta_6$ in a metal dependent manner (Ca(II), Mg(II), FIG. 5, FACS data). We measured binding on the yeast surface using 4 different concentrations of biotinylated $\alpha_v\beta_6$ (50 pM, 100 pM, 300 pM and 500 pM, supplementary information). av6_3 showed the highest binding signal for $\alpha_v\beta_6$ based on yeast surface display experiments (FIG. 6) and bound more tightly than the original crystallized variant. We expressed and purified 5 strongest binders ((av6_3, av6_7, av6_9, av6_11 and av6_15) in *E. coli.* and deter-mined that av6_3 shows highest level of selectivity towards $\alpha_v\beta_6$ as compared to $\alpha_v\beta_8$, another integrin responsible for TGF-β activation (FIG. 7). In av6_3, the canonical RGDLXXL (SEQ ID NO:32) motif of the prodomain of TGF-β1 is incorporated in the loop connecting Sheet1 and Helix1 of the ferredoxin fold (FIG. 1*g*). The amphipathic helix following the RGD loop packs against the hydrophobic groove formed by the 06 subunit (FIG. 1*h*) mimicking the binding interactions of the TGF-β1 peptide to $\alpha_v\beta_6$. Asn37 forms a hydrogen bond with Asp901 from β6 subunit, and Arg61 hydrogen bonds to the backbone atoms connecting residue Ser756 and Ile757 of $\alpha_v\beta_6$ (FIG. 1*i*). All the residue numberings are based on Rosetta™ internal numbering system starting from the first residue of the designed binder.

Figure 2:
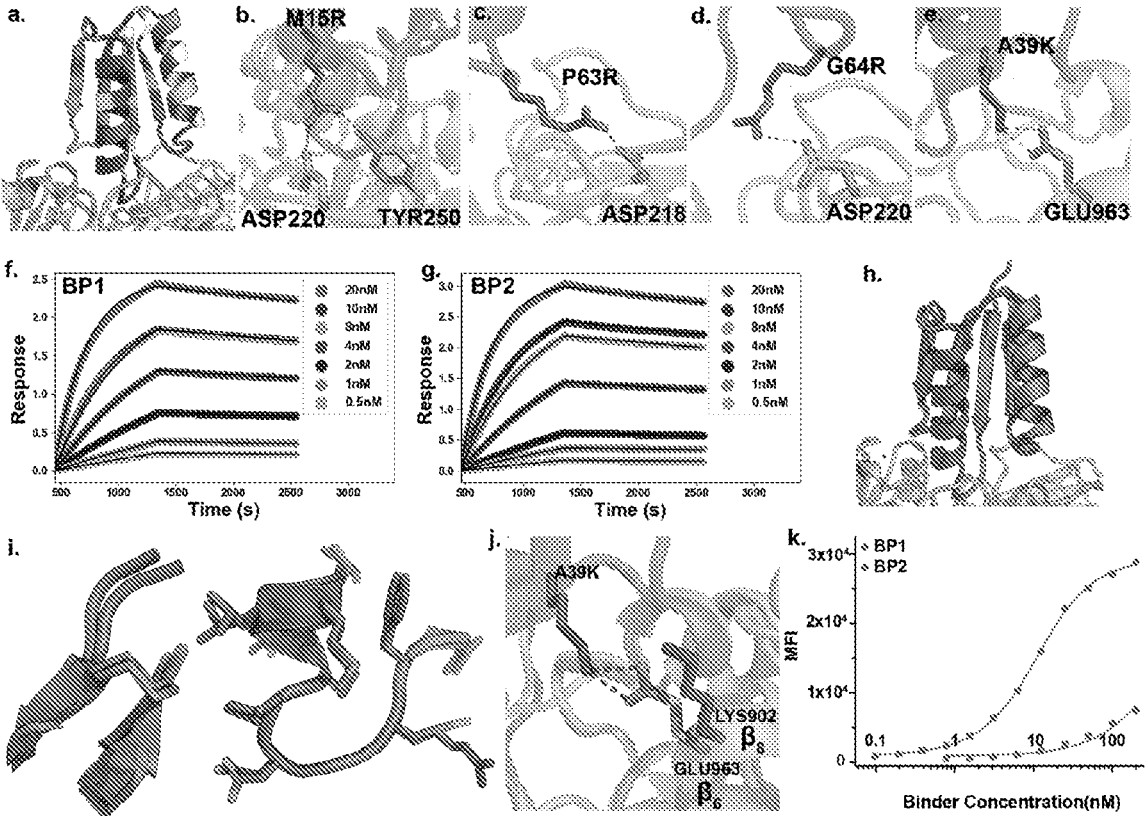
FIG. 2a-k. a. Site saturation mutational analysis of the designed binder: b-e. Most of the enriched variants are charge-complementary to the receptor (see main text for details). f,g. BLI titrations of purified BP1 and BP2 against $\alpha_v\beta_6$. Kd for both these mutants are <1 nM, each titrations were carried out at least twice with similar results. h. Crystal structure of BP1_disulf superimposed on the designed model (binder, $\alpha_v\beta_6$). i.j. Superposition of the designed model of the disulfide bond and the RGD loop region with the crystal structure k. The A39K mutation confers specificity towards $\alpha_v\beta_6$ as compared to $\alpha_v\beta_8$ where there is a charge reversal (Glu963 for 06 and Lys902 for 08 shown). L. Cell surface titration of BP1 and BP2 against K562 cells stably transfected with $\alpha_v\beta_8$. BP1 lacking the A39K mutation binds to $\alpha_v\beta_8$ with a Kd of ~7.3 nM whereas BP2 containing the A39K mutation binds to $\alpha_v\beta_8$>500 nM.
Figure 8:
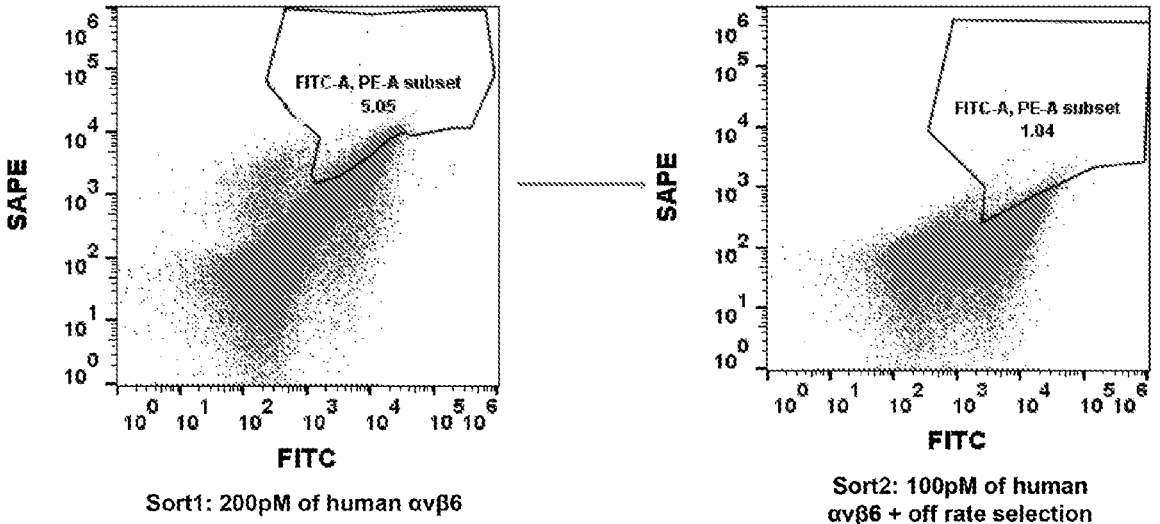
FIG. 8. Sorting scheme for the SSM-library of av6_3. First Round of Sorting was done at 200 pM of v06 followed by final sort using 100 pM receptor.

To probe the sequence determinants of binding, every residue in design av6_3 was mutated to each of the other 19 amino acids, and two rounds of yeast surface display and FACS sorting for $\alpha_v\beta_6$ binding were performed (FACS, FIG. 8). Deep sequencing of the pool before and after selection identified substitutions that were enriched upon binding selection; (see Tables 1-3). The core residues of the lead $\alpha_v\beta_6$ mini binder are largely conserved, suggesting the designed residues are close to optimal for folding (FIG. 2*a*). Mutations to the RGD loop are, as expected, highly depleted given the importance of this tripeptide motif for binding. There are mainly 5 enriched mutations in the interface: 2 of the mutations (E13/A39) interact with the β6 subunit, One mutation, M15 is in between the groove formed by the $\alpha_v$ and β6 subunit and P63/G64 interacts with the $\alpha_v$ subunit. Immediately following the amphipathic helix, E13 prefers to be hydrophobic or small polar residues likely due to proxi-mal negatively charged residues on the integrin; the threo-nine enriched at this position is also present in the TGF-β1 peptide. Most of the other highly enriched substitutions also involve charge-complementarity: M15R/K is well within hydrogen bonding interaction range to D220 and Y250 of v06 (FIG. 2*b*). Two consecutive residues (P63 and G64) on loop2 facing the $\alpha_v$ subunit are enriched as positively charged Lys or Arg residue, which likely form salt bridges with two acidic residues D218 and D220 on the $\alpha_v$-subunit of the receptor (FIGS. 2*c* and 2*d*). The A39K substitution facing the β6 subunit likely introduces a salt bridge with Glu963 (FIG. 2*e*). We expressed, purified and tested a total of 9 mutants of these selected substitutions alone and in combination using biolayer interferometry (BLI) measure-ments. All the variants showed subnanomolar binding affinity towards $\alpha_v\beta_6$, whereas the original unevolved av6_3 binds to $\alpha_v\beta_6$ with a Rd of 1.18 nM (See Table 5). Two high affinity variants were selected for further characterization: BP1 (av6_3_ET3T) with a single substitution that more closely recapitulates the TGF-β1 peptide sequence and BP2 (av6_3_A39KG64R) with two substitutions introducing positive charges complementing negative charges in both subunits of the $\alpha_v\beta_6$ integrin.

TABLE 5

| Mutants | Sequence | Kd (nM) |
|---|---|---|
| E13T | (SEQ ID NO: 21) | 0.334 |
| M15R | (SEQ ID NO: 20) | 0.38 |
| A39K | (SEQ ID NO: 22) | 0.411 |
| G64R | (SEQ ID NO: 23) | 0.47 |
| E13TG64R | (SEQ ID NO: 26) | 0.398 |
| M15RG64R | (SEQ ID NO: 24) | 0.404 |
| A39KG64R | (SEQ ID NO: 25) | 0.414 |
| E13TM15RA39K | (SEQ ID NO: 27) | 0.397 |
| E13TM15RA39KG64R | (SEQ ID NO: 28) | 0.42 |

Functional Characterization of the Designed Inhibitors:

TGF-β is produced as an inactive complex with a latency associated peptide (LAP); $\alpha_v\beta_6$ binds to this inactive LAP: TGF-β complex and releases active TGF-β. This active TGF-β then interacts with TGF-βRI/RII and triggers down-stream signaling. The expression of $\alpha_v\beta_6$ is restricted pri-marily to epithelial cells, and under normal physiological conditions is largely limited to tissues undergoing morpho-logical changes during development, with little or no expres-sion in fully differentiated epithelia. However, in pathologi-cal conditions, $\alpha_v\beta_6$ expression is upregulated upon tissue reprogramming during tumor cell migration, wound healing, and inflammation, and high levels of $\alpha_v\beta_6$ expression are associated with poor overall survival in a wide range of cancers including non-small cell lung cancer (NSCLC) and pancreatic cancer. This also garnered a significant interest in targeting $\alpha_v\oplus_6$ in immune-oncology.

We set out to test the ability of these binders to bind to $\alpha_v\beta_6$(+) cells and block TGF-β mediated downstream sig-naling. We generated fluorescently labelled BP1 and BP2 by conjugating Alexafluor-488 to an engineered C-term cyste-ine via maleimide chemistry. The fluorescently labelled proteins were titrated against $\alpha_v\beta_6$ positive human epider-moid carcinoma A431 cells. BP1 and BP2 bind to A431 cells with $K_d$ values of 167 (±0.028) pM and 30 (±0.004) pM respectively (data not shown).

Figure 3:
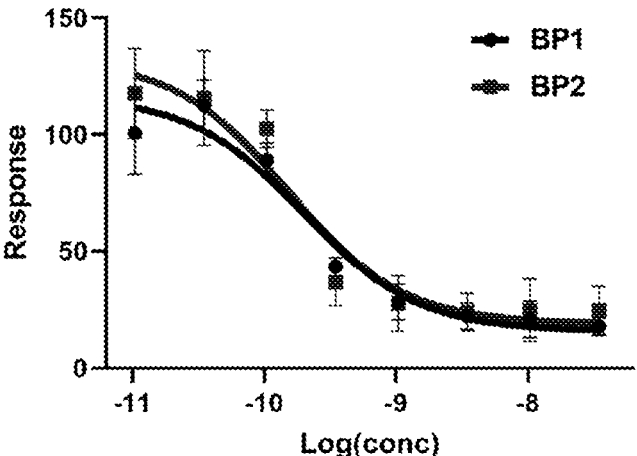
FIG. 3. TGF-β inhibition mediated by BP1 and BP2 in TMLC assay. Both BP1 and BP2 blocks $\alpha_v\beta_6$ mediated TGF-β activation with similar IC50 (199 pM and 151 pM respectively)

Next, we investigated the ability of these designed binders to block TGF-β signaling using transformed mink lung reporter cells (TMLC), which produce luciferase in response to active TGF-β. Both BP1 and BP2 block $\alpha_v\beta_6$ mediated TGF-β activation with an $IC_{50}$ values of 199 pM (95% CI [119 pM, 332 pM]) and 151 pM (95% CI [79.6 pM, 284 pM], respectively (FIG. 3). BP1 also blocks $\alpha_v\beta_8$ mediated TGF-β activation, whereas BP2 has no effect at the highest concentration tested (333 ng/ml), consistent with their in vitro binding profiles (FIG. 10).

As BP2 binds to A431 cells with higher affinity and is more specific towards $\alpha_v\beta_6$ as compared to BP1, we selected BP2 for further in vivo experiments. To investigate whether the evolved variants can bind to $\alpha_v\beta_6$ (+) tumors in vivo, we generated a fluorescently labelled BP2 (AF680-BP2) via an engineered C-term cysteine by chemically conjugating it to Alexafluor-680 C-2 maleimide. 6-8 week old female athy-mic nude mice were injected with A431 cells $\alpha_v\beta_6$ (+)) and HEK 293T ($\alpha_v\beta_6$(-)) into the left and right shoulders, respectively. When the tumors reached 5-10 mm in diameter, mice were injected with 1.5 nmols of AF680-BP2 proteins. AF680-BP2 rapidly accumulates in the $\alpha_v\beta_6$ positive tumors and reaches an excellent tumor-to-muscle fluorescence contrast ratio within 3 hours post-injection (data not shown). There was no detectable fluorescence at the $\alpha_v\beta_6$ negative HEK-293T tumors, demonstrating selectivity towards $\alpha_v\beta_6$ in vivo. We also performed a semiquantitative ex vivo biodistribution analysis of AF680-BP2. Analysis of fluorescence intensities of different tissues revealed accumulation of AF680-BP2 to $\alpha_v\beta_6$ positive tumors and kidney (tumor-to-kidney ratio 1:1.04, data not shown) with no significant off-target binding including $\alpha_v\beta_6$ negative tumors. These results clearly demonstrate selective targeting of $\alpha_v\beta_6$ positive tumors in vivo using designed binders. Moreover, quantification of whole body imaging data for AF680-BP2, following tail vein injection suggests it has an approximate serum half-life of <2 hours (data not shown) and that its elimination can be through glomerular filtration via the kidney into the urine, and by liver metabolic processes.

Determinants of Specificity of the Designed Binder Against Other RGD-Binding Integrins:

As noted above, Integrin $\alpha_v\beta_8$ also plays a role in the activation of TGF-β1/TGF-β3. $\alpha_v\beta_8$ is overexpressed on T-reg cells and essential for suppressing T-cell mediated inflammation. For therapeutic applications, it is desirable to inhibit $\alpha_v\beta_6$ mediated TGF-β inhibition as compared to global inhibition of TGF-β. In BP2, loop2 is positioned to confer specificity between the two integrins (FIG. 2j): K39 in loop2 faces E963 in the $\beta_6$ subunit and K901 in $\beta_8$ (FIG. 2j). BP2 discriminates against $\alpha_v\beta_8$, with a >5000 fold specificity towards $\alpha_v\beta_6$ on cell surface binding assay using K562 cells stably expressing $\alpha_v\beta_6/\alpha_v\beta_8$. BP1, which has an alanine (A39) at this position, has much lower specificity (FIG. 2k). BP1 and BP2 do not cross react with other RGD-binding integrins including $\alpha_v\beta_1$, $\alpha_v\beta_3$, $\alpha_v\beta_5$, $\alpha_5\beta_1$, $\alpha_8\beta_1$, and $\alpha_{iib}\beta_3$ (at concentrations up to 200 nM in cell surface binding experiments using K562 cells stably transfected with different RGD-binding integrins.

Figure 9:
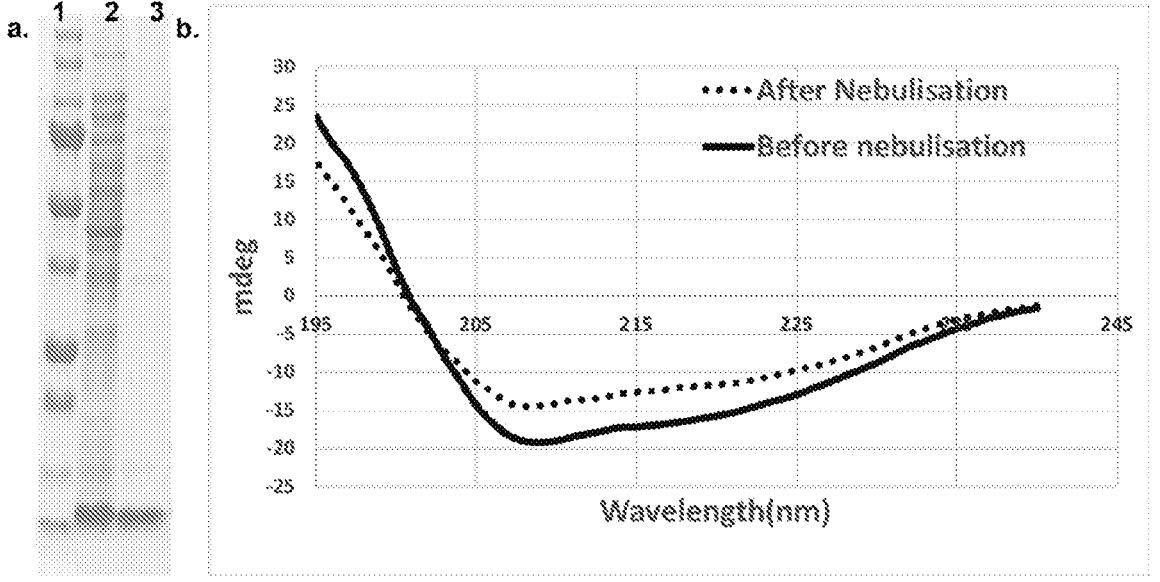
FIG. 9a-b. a. SDS page gel for one step purification of BP2_disulf from cell lysate by heat treatment. Lane1: ladder, Lane2: BP2_disulf crude cell lysate. Lane 3: BP2_disulf cell lysate after boiling at 85° C. for 10 mins. b. CD spectra of BP2_disulf before and after nebulization.

To further increase protein stability, we used Rosetta™ to scan pairs of positions on the designs to introduce a disulfide bond with optimal geometry, and selected four variants (two for each construct) for experimental characterization. Both versions of the proteins with or without the disulfide bond elute as a single monodisperse peak by size exclusion chromatography. Circular dichroism (CD) spectra of the designs show two minima centered around 208 and 222 nm consistent with a mixed alpha/beta fold (data not shown). Introduction of the disulfide bond made both proteins hyperthermostable, maintaining their secondary structure at 95° C. suggested by CD spectroscopy data under non-reducing conditions (data not shown). We chose two of these proteins (BP1_disulf and BP2_disulf here on) for further in vitro and in vivo characterization. Both BP1_disulf and BP2_disulf can be purified in a single step from E. coli cell lysate by boiling at 85° C. for 10 mins FIG. 9). BP2_disulf binds to $\alpha_v\beta_6$ with subnanomolar affinity and knockout mutation of the RGD to KGE abrogates binding to the receptor confirming that the RGD loop is necessary for binding.

We solved the crystal structure of a disulfide stabilized version of BP1 that binds to $\alpha_v\beta_6$ with subnanomolar affinity and does not melt at 95C, BP1_disulf, at XX A RMSD. The crystal structure matches the design model very closely with root mean square deviations (r.m.s.d.) of 0.54 Å (FIE. 2h). In the crystal structure, the disulfide bond also adopts similar conformation as the designed model (FIG. 2i). The majority of the core hydrophobic residues adopt rotamers identical to the design model. Unlike most of the designed protein inhibitors, most of the interactions in BP1_sulf are mediated by loops. There are three loops that make contact with $\alpha_v\beta_6$: 1) RGD loop 2) Loop1 and 3) Loop2 (FIG. 2f). The designed RGD binding loop is 5 residues long and adopts nearly identical backbone conformation as the designed model (FIG. 2j). All the residues on the loop adopt similar rotamers as the designed model with the exception of the Arginine (FIG. 2j). Immediately followed by the RGD loop, the LATL motif forms an amphipathic helix that can pack against the hydrophobic groove on the $\beta_6$ subunit. Previously, it has been shown that $\alpha_v\beta_6$ not only recognizes the RGD loop but also an amphipathic helix formed by LXXL (SEQ ID NO:33) motif that interacts only with the $\beta_6$ and provides the blueprint of ligand binding specificity and recognition beyond the RGD sequence. Loop1 connecting sheet 2 and sheet 3 makes contact with the 06 subunit and is designed to adopt GGGA abego type. Loop2 connecting helix2 and sheet4 makes contact with $\alpha_v$ subunit (FIG. 1f) designed to be BAAB abego type. In the crystal structure, both of these loops adopt near identical backbone conformations to the design model (FIG. 2h). In the design model of the complex, Asn37 on loop1 hydrogen bonds with Asp901 from the 06 subunit of the receptor, and is within coordinating distance to the Ca(II) atom in $\alpha_v\beta_6$, which is absent in the case of $\alpha_v\beta_8$. In the designed structure, Loop1 is ideally positioned to confer specificity towards the 3 subunit and provides easy access to integrin subtype specific designed inhibitors.

BP2-Disulf Decreases the Fibrotic Burden of Bleomycin Challenged Mice and Restores Lung Function:

IPF is progressive disease characterized by the formation of scar tissue within the lung, which has a median survival time from diagnosis of 3 to 5 years. Patients experience progressive shortness of breath and lung function impairment measured as decreased forced vital capacity (FVC), decreased diffusion, decreased oxygenation and ultimately respiratory failure. Progression in lung fibrosis is in part due to the exacerbation of the Smad 2/3 pathway by $\alpha_v\beta_6$ integrin activation of TGF-β. After confirming BP2 can specifically block $\alpha_v\beta_6$ mediated TGF-β signaling in TMLC assay, we investigated the therapeutic efficacy of this molecule in bleomycin induced pulmonary fibrosis in mice.

Male 12 week-old C57BL/6 mice were intratracheally instilled with 50 μL of bleomycin (1 mg/kg body weight). Mice were injected intraperitoneally with BP2_disulf binder every other day starting at day 7 post bleomycin instillation and ending on day 19 for a total of 7 treatments administered as compared to the non-treated (data not shown). There is loss in body weight (approximately 5-8% of initial weight) in bleomycin (BLM and bleomycin with BP_2disulf treatment as compared to the NY group (data not shown). However, BP2_disulf treatment reduces the overall weight loss 14 days post-lung injury as compared to the BLM group (data not shown). High-resolution lung scans of mice were obtained using a micro-CT scanner and allowed for real-time visualization of the development of fibrosis. Damage to the lungs can be seen as early as day 7 and is pronounced in days 14 and 21 (data not shown). With BP2_disulf treatment, by day 21 the lung tissue did not develop the large fibrotic lesions that were prevalent in the BLM mice (data not shown). BP2_disulf treated mice did have damage due to the bleomycin challenge, but the lesions were not as exacerbated as the BLM group. The lung morphology of the BP2_disulf treated mice show fibrotic lesions but maintains the alveolar air-spaces which are not present in the bleomycin challenged mice (data not shown). Non-treated mice exhibited a fibrotic burden of 4.107%, bleomycin challenged mice 11.01% and BP2_disulf treated mice 6.857% (data not shown). BP2_disulf and NT mice have a significantly lower fibrotic burden compared to the BLM group. Frequency of tissue density was collected by dividing Hounsefield Unit intensities into bins and sampling the scan images for frequency of bin intensities. Distribution of the tissue density shows a shift to the right for bleomycin-injured mouse scan images indicating an increase in dense tissue compared to NT and BP2_disulf treated groups of mice. BP2_disulf treated and NT distributions are comparable (data not shown).

To confirm that BP2_disulf not only reduces bleomycin induced fibrotic burden, but also improves overall lung function as compared to the NT group, 21 days post bleomycin administration, lung mechanics were measured using a FlexiVent™ FX system. Static compliance measures the elastic properties of the lungs and is calculated from pressure-volume loops. BP2_disulf treatment induced a statistically significant increase of static compliance over mice treated with bleomycin alone (data not shown), with similar elastic properties to the non-treated mice. Forced Vital Capacity (FVC) in BP2_disulf treated mice showed similar air flow to the NT mice with statistically significant increase over BLM mice (data not shown). BP2_disulf treatment rescues lung function losses due to the bleomycin-induced IPF-like restrictive lung disease. Average PV loop calculations show nearly indistinguishable differences to NT mice with 100% improvement over bleomycin mice (data not shown).

Discussion

The designed inhibitor (BP2_disulf) described here binds to $\alpha_v\beta_6$ with high affinity and specificity. The protein contains a single disulfide bond is hyper-thermostable, is easily expressed in *E. coli* with high yield and can be purified from crude cell lysate in one step by heating at 85° C. (FIG. 10). BP2_disulf is highly efficacious in the bleomycin-induced IPF mouse model (100 pG/kg). Mice treated every other day via intraperitoneal injection showed improved lung mechanics and histopathologic changes. The protein shows promising results as an inhaled therapy for bleomycin induced IPF model (supplementary information). Due to the high thermal stability of the protein, it can also be formulated as nebulized treatment. BP2_disulf maintains its secondary structure after nebulization (FIG. 10). This is particularly advantageous because of limited tissue specific exposure of the binder as compared to global inhibition of TGF-β as in the case of IP injection. The short serum half-life (<2 hours), high specificity and affinity for $\alpha_v\beta_6$ target binding, ease of production using *E. coli*, hyper-thermostability, aerosol formulatability of our designed mini-binding proteins, offer an improved target product profile as novel candidate therapies for IPF. In contrast to antibody inhibitors, the $\alpha_v\beta_6$ binders disclosed herein can be formulated for tissue specific delivery with built-in tunable serum half-life and reduced systemic exposure, both factors which are expected to improve safety and reduce the chance of unwanted side effects (e.g. the lung residence and short serum half-life of an aerosol $\alpha_v\beta_6$ binder therapy for IPF could support better outcomes in eventual lung transplant settings for IPF patients). The recent outbreak in SARS-COV-2 also presents a severe threat to pulmonary health of the older population. Although the majority of the affected populations recover without any major complications, patients with ARDS develop severe lung damage/lesions and are expected to develop pulmonary fibrosis over time as in the case of the last SARS outbreak. Hence, the de novo designed protein reported here has considerable therapeutic potential in treating IPF, as well as the progressive respiratory disease associated with current and future coronavirus infection as well as cancer immunotherapy.

A frequent challenge in drug development is the targeting of a single member of a large family of closely related proteins. This can be difficult to achieve with small molecules, and the development of antibody panels capable of such discrimination can be challenging as considerable amounts of negative selection are likely required. Our structure-based de novo design strategy provides a systematic way to achieve such specificity, integrating in a hyperstable small scaffold both previously known binding motifs and completely new interactions, which confer higher affinity and specificity between $\alpha_v\beta_6$ and $\alpha_v\beta_8$. The ability to combine features such as the RGD loop and the specificity conferring additional loop containing K39 in a minimalist stable scaffold is a considerable advantage of computational design over previous approaches.

Materials and Methods

Computational Techniques: Overview of the design protocol has been discussed in the main text.

Yeast Display: Standard yeast surface display techniques were used to screen designs for binding and directed evolution. Genes encoding the designs were cloned into petcon2 in frame with N-term aga2 and C-term myc tag. Surface expression of Myc was detected using Anti-C Myc antibody and binding was detected by using biotinylated human $\alpha_v\beta_6$ and stained with phycoerythrin conjugated streptavidin for FACS. Two different buffers were used for the binding and washing steps for yeast display: Binding Buffer 20 mM TRIS, 150 mM NaCl, pH=8.0, 1% BSA, 1 mM Ca(II) and 1 mM Mg(II), Wash Buffer: 20 mM TRIS, 150 mM NaCl, pH=8.0, 0.5% BSA, 1 mM Ca(II) and 1 mM Mg(II).

The SSM library was generated by using mutagenic primers (see below for sequences) for each position following a previously described protocol. The resulting library was transformed into yeast using electroporation in duplicates (biological replicate). The sorting was performed in two rounds: The library was first treated with 4 uM Trypsin and 0.8 uM chymotrypsin for 5 mins followed by labelling with 200 pM of biotinylated $\alpha_v\beta_6$ and top 5% of the binders were collected. For the second and final round of selection, 100 pM of biotinylated $\alpha_v\beta_6$ was used along with an off rate selection. For the off rate selection step, 500 nM of the unevolved purified av6_3 was added to the cells and tumbled at 37C for 1 hour and the top 1% of the binding population was selected (FIG. 8). DNA was extracted from pre and post sorted pools and barcoded. Enrichment ratios are calculated after sequencing the pools using Illumina.

Protein Expression and Purification: Genes encoding protein variants were ordered as gblock gene fragments from IDT and cloned in pet29b in between NdeI/XhoI restriction sites with a C-term Histag. All the mutant variants of the proteins were expressed in BL21(DE3*) using Studier Autoinduction technique in standard shake flasks at 25° C. for 36 hrs. Cells were harvested and resuspended in 20 mM Tris, 250 mM NaCl, 20 mM Imidazole (lysis buffer). Cells were lysed using microfluidizer and cell debris was separated by centrifuging at 24000 g for 45 mins. Soluble proteins were first purified using standard Ni-NTA affinity columns followed by size exclusion chromatography (S75 10/300 increase) on a GE-Akta pure FPLC system. Peak corresponding to the monomeric protein was collected and further verified by mass spectrometry. For bleomycin induced IPF models, protein was subjected to further purification to achieve endotoxin level <5 EU/ml.

Biotinylation of Designed proteins: To generate mono-biotinylated proteins, avi-tag sequence (GLNDIFEAQK-IEWHE; SEQ ID NO:34) was introduced to the N-term of the proteins. Proteins were biotinylated either by co-transforming protein of interest along with pBirA, a vector encoding *E. Coli* biotin ligase for in vivo biotinylation or using purified protein and an in vitro biotinylation kit form Avity using manufacturer's protocol. Biotinylation was further confirmed via mass spec.

Structural Analysis of the Designed Proteins:

For determining the crystal structure of BP1_disulf, we expressed BP1_disulf with a Nterm-TEV cleavable histag. After protein expression and purification, BP1_disulf was treated with (1/100) dilution of stock TEV protease and left and processed using XDS. Intriguingly, the diffraction data of binding protein were originally scaled to $P6_122$ space group with large Patterson peak 1/3 and 2/3 c axis indicating two translational NCS molecules along the c axis. Solution was found using the designed model. Model was refined in Rosetta™ and then rebuilt with phenix.autobuild. Autobuild was able to rebuild most sequences of the model, but R and Rfree are still very high, at 44%/47% with reasonably good electron density maps. Then Data was re-scaled to $P3_1$ space group and refined the structure, which contains 12 molecules per asymmetric unit, with tetrahedrally twinning. AUTO-BUILD™ was used to build one-third of the sequence and was used several times in the first few of many iterative steps of manual building in COOT and refinement with PHENIX™ and RefMAC™. MolProbity™ was used to validate the final structure.

TABLE 6

| Statistics of X-ray diffraction and structure refinement | | |
| --- | --- | --- |
| | BP | BP1_disulf2(E13T_disulf2) |
| Data collection statistics | | |
| Space group | $P3_1$ | $P2_12_12_1$ |
| a, b, g, ° | 90, 90, 120 | 90, 90, 90 |
| Unit cell (a, b, c), Å | 92.3, 92.3, 82.4 | 40.7, 64.1, 81.0 |
| Resolution range (Å) | 50.0-1.90 (1.97-1.90) [a] | 50.0-1.80 (1.85-1.80) |
| Completeness (%) | 99.9 (99.8) | 98.9 (100.0) |
| Number unique reflections | 55,726 (3,570) | 20,120 (1,497) |
| Redundancy | 5.6 (4.5) | 6.0 (6.3) |
| $R_{merge}$ (%) [b] | 9.3 (61.3) | 8.7 (129) |
| I/s(I) | 10.4 (2.4) | 13.5 (2.5) |
| $CC_{1/2}$ (%)[c] | 99.6 (11.4) | 99.5 (73.9) |
| Wavelength (Å) | 1.0332 | 1.0332 |
| Refinement statistics | | |
| $R_{work}$ (%)[d] | 20.2 | 23.5 |
| $R_{free}$ (%) | 24.2 | 27.3 |
| Bond RMSD (Å) | 0.005 | 0.003 |
| Angle RMSD (°) | 0.71 | 0.51 |
| Ramachandran plot[e] (Favored/allowed/outlier) | 96.1/3.9/0.0 | 98.6/1.4/0.0 |
| Number of atoms | | |
| Protein | 6369 | 1779 |
| Ligand | 6 | 0 |
| Water | 331 | 112 |
| Molprobity percentile (Clash/Geometry) | 99/99 | 98/99 |
| PDB | | |

[a] The numbers in parentheses refer to the highest resolution shell.

[b] Rmerge = Sh Si |(Iih) − <I(h)> |/ShSi Ii(h), where Ii(h) and <I(h)> are the ith and mean measurement of the intensity of reflection h.

[c]Pearson's correlation coefficient between average intensities of random half-datasets for each unique reflection[28].

[d]Rfactor = Sh||Fobs (h)| − |Fcalc (h)||/Sh|Fobs (h)|, where Fobs (h) and F calc (h) are the observed and calculated structure factors, respectively. No I/s(I) cutoff was applied.

[e]Calculated with MolProbity[18].

overnight at room temperature dialyzing against TBS. Following the completion of the cleavage monitored via SDS-page gel, proteins were run over a second gravity Ni-NTA column to separate cut his-tag and his-tagged-TEV from cleaved protein. Following the histag cleavage proteins were concentrated to ~50 mg/ml and setup for crystallization trials. Binding protein and BP1_disulf were crystallized by vapor diffusion at 24° C. by mixing with an equal volume of reservoir solution: 0.2 M $KNO_3$, 20% PEG3350 and 0.2 M K3Citrate, 20% PEG3350 respectively. Crystals were briefly cryo-soaked in a reservoir solution containing 15% PEG200 and flash-frozen in liquid nitrogen. Diffraction data were collected at the GM/CA beam line of Advanced Photon Source (APS) at −173° C. using a MAR225 CCD detector Biophysical Characterization of the Designed Protein:

Protein secondary structure and thermal stability were measured using JASCO-1500 CD instrument. For normal wavelength scan, 10-15 uM of protein in TBS (20 mM TRIS, 50 mM NaCl, pH=8.0) was used. The CD spectra was measured from 240-195 nm with a scan rate of 100 nm/min. For thermal melt experiments, signal intensity at 222 nm was monitored as a function of temperature (4° C.-95° C.) with a temperature gradient of 2° C./min. The sample was held at the specified temperature for at least 5 sec before measurement. To investigate the role of the engineered disulfide bond on stability, 1 mM TCEP was added to the protein to measure thermal stability under reducing condition.

Biolayer Interferometry for Determining Binding Kinetics of the Proteins:

Data was collected on an Octet™ RED96 (Forte Bio) and processed using the instrument's software. His Tagged protein binders were immobilized on Ni-NTA octet sensors. The tips are then dipped into wells containing different concentrations of $\alpha_v\beta_6$. Association and dissociation steps were recorded for 900 s and 1200 s respectively. An empty sensor with no loaded binding protein was included to discard any non-specific binding of $\alpha_v\beta_6$ to the octet tip.

Fluorescent Labelling of Designed Binders:

For in vitro binding assay and in vivo imaging experiments, designed binders were labelled with Alexa Fluor™ 488 C5 Maleimide and Alexa Fluor™ 680 C2 Maleimide (Thermo Fisher Scientific), respectively, via a C-term single cysteine variant. In a typical labelling experiment, 50-200 uM of proteins were reduced with 1 mM TCEP for 30 minutes at room temperature. 3-5 molar excess of the maleimides were added to the protein solution and tumbled at room temperature overnight. The reaction mixture was then purified on a S75 increase 10/300 column to separate free dye from the labelled proteins. Fluorophore conjugation was further confirmed by mass spectrometry.

In Vitro Binding Assays Using Fluorescently Labelled Binders:

Epidermoid cancer cells (A431) and human embryonic kidney 293T cells (HEK 293T) were purchased from American Type Culture Collection (ATCC) and grown in Dulbecco's Modified Eagle Medium (DMEM, Gibco) supplemented with 10% fetal bovine serum (FBS, Gibco) in a humidified atmosphere with 5% $CO_2$ at 37° C. Binding assays were performed on A431 carcinoma cells. A431 cells were dissociated from culture flasks with enzyme-free cell dissociation buffer (Gibco). Varying concentrations of AG-AF488 and E13T-AF488 were incubated with 5×104 A431 cells in 1×TBS with 0.1% BSA, 1 mM Ca2+, and 1 mM Mg2+(BTBS) rotating in suspension for 5 hours at 4° C. Sufficient incubation volumes were used to avoid >5% ligand depletion. After incubation, cells were washed with BTBS and analyzed by flow cytometry on an Accuri™ C6 instrument (BD Biosciences), and data were quantified using FlowJo™ software (TreeStar). Kd values were determined by fitting the data to a one site-specific binding curve using Prism™ 7 (GraphPad Software).

Inhibition of $\alpha_v\beta_6$ mediated TGF-$\beta$ Activation by Designed Inhibitor Using TMLC Assay:

Commercial source and description of the reagents used for TMLC assays are given in Table 7.

TABLE 7

| Reagent/Kit/Cells | Initiation/Supply | Passage prior to plating | Comments |
|---|---|---|---|
| TMLCs (Nottingham University) | Initiated 1 vial per flask 22 Jan. 2018. | P2 | Cultured in DMEM (Gibco 41966) supplemented with 10% FBS and G418 (0.2 mg/ml) |
| HeLa b8 cells | Supplied in culture by core TC. Last split 23 Jan. 2018 | P4 | Cultured in MEM (Gibco, 31095-029), 10% FBS, 1% NEAA |
| K562 parental (AZ) | Initiated 12 Jan. 2018. Last split 24 Jan. 2018. | P8 | Cultured in RPMI (Gibco 61870), 10% FBS, 1% NaPy + pen/strep |
| K562 avb6 transfected clone A4 | Initiated 12 Jan. 2018. Last split 24 Jan. 2018. | P7 | RPMI, 10% FBS, 1% NaPy, 1 mg/ml G418 |

33

Recombinant human TGFb1 (R&D Systems, cat. 240-B-010)

Luciferase assay system (Promega, cat. E1501) Used according to manufacturer's protocol Reporter lysis buffer 5× (Promega E397A)

96-well cell culture plates (Costar cat. 7107)

96-well white bottom, white walled, polystyrene Opti-plates™ (Perkin Elmer 6005290)

Antibodies anti-TGFb1, 2, 3 mIgG1 clone 1D11 (R & D Systems MAB1835-500) 0.5 mg/ml mouse IgG1 isotype control clone 11711 (R & D Systems MAB002) 0.5 mg/ml anti-av (CD51) mIgG1 clone L230 (Enzo ALX-803-304-C100) 0.1 mg/ml anti-avb6 3G9 (in-house) hIgG1 SP16-106 10.21 mg/ml NIP228 hIgG1 (isotype for 3G9) (in-house)

Anti-avb8 (in-house)

NIP228 hIgG1 (isotype for anti-avb8) (in-house)

Anti-avb6/b8 264RAD (in-house) BPD.95 SP10-362 10.45 mg/ml

Detailed protocol for TMLC assay:

Co-Culture Assay Set-Up

Assay media: DMEM+1% FBS+Pen/strep

1. Remove TMLCs cells 1LF from the flask using accutase.
   Wash in 10 ml PBS and add 5 ml accutase/flask
   Incubate at 37° C. for 3-5 mins
   Add assay media and spin 300× g 5 minutes
   Suspend in 5 ml assay media and count
   3.3e6 ml. 1.65e7 total
   Suspend in 55 ml assay media
2. After counting using trypan blue exclusion suspend cells in assay media at a concentration of 300 000 cells/ml.
3. Add 50 ul of cell suspension per well (15 000 cells/well) to appropriate wells of a 96 well tissue culture plate (see plate layout).
4. Leave cells for 3 hours for TMLCs to adhere
5. Prepare abs and binding proteins at 2× final concentration
6. Add 200 ul abs, binding proteins or media to appro-priate wells in a 96 well deep well pp plate
7. Prepare 2 ng/ml rhTGF-b1 in assay media
   Stock is 20 ug/ml: 10,000-fold dilution (1/100 then 1/100)
   2 ul+198 ul media
   15 ul (1/100)+1485 ul media
Prepare cells at 2× concentration.

34

1) Remove HeLa b8 cells from the flask using accutase. After counting using trypan blue exclusion suspend cells at 300,000 cells/ml).
   2.52e6/ml. 1.263e7 total suspend in 42.1 ml
2) Take approximate number of K562 parental and avb6 transfected cells required (30 ml) and spin 300× g for 5 minutes. Resuspend cell pellets in 5 ml assay media and count. Suspend cells at 1.2×10⁶/ml.
   K562 parent 4.25e6 ml 2.125e7 total. Suspend in 17.7 ml
   K562avb6 2.725e6 ml 1.36e7 total. Suspend in 11.4 ml.
3) Add 200 ul cells or media or 2× rhTGF-b1 to appro-priate wells containing binding proteins, antibodies or media in the deep well pp plate (see step 6).
4) Incubate for 15 minutes at room temperature to allow binding proteins/antibodies to bind cells/TGF-b).
5) Aspirate media and add 100 ul/well cells+/−Abs, media or 1 ng/ml rhTGF-b1+/−abs to appropriate wells (see plate layout).
6) Incubate cells at 37° C., 5% C02 for 18-20 hours before measuring luciferase activity.

Luciferase Assay

1. Remove 70 ul culture supernatant using multichannel and store in 96 well u bottom polypropylene plates at −80° C. for potential later analysis of cytokines/MMPs.
2. Wash cells twice with 200 ul/well PBS (aspirate between washes) doesn't matter if lose the K562 cells.
3. Add 100 ul of 1× reporter lysis buffer (1 part 5× lysis buffer+4 parts distilled water) to each well and freeze thaw the cells in the −80 freezer to fully lyse the cells.
4. Prepare luciferase assay buffer by thawing out the luciferase assay buffer to room temperature and then add this to the lyophilized luciferase assay substrate.
5. Transfer 80 ul of cell lysate to a white walled clear bottom plate and add 100 ul of luciferase assay reagent.
6. Read the signal immediately on a luminometer.
   Envision ultra-sensitive luminescence (96) assay Statistical Analysis All values were reported as mean±SD. Data were ana-lyzed by one-way ANOVA followed by Tukey's post-hoc test for multiple comparisons. Analysis and graphs were done with GraphPad™ Prism 6.0 (GraphPad, San Diego, CA. USA). Results with p-value<0.05 were considered statistically significant.

Sequences of the all Designs and Evolved Variants Reported in this Paper: See Table 4

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

We claim:

1. A polypeptide comprising the amino acid sequence selected from the group consisting of SEQ ID NOS:4-30 and 36, and wherein the polypeptide binds to alpha(v) beta (6) integrin (avb6).

2. The polypeptide of claim 1, wherein the polypeptide comprises the amino acid sequence selected from the group consisting of SEQ ID NOS:4-30.

3. The polypeptide of claim 1, wherein the polypeptide comprises the amino acid sequence selected from the group consisting of SEQ ID NOS: 4, 6, 7-8, 10-12, 14-16, 18, and 20-30.

4. The polypeptide of claim 1, wherein the polypeptide comprises the amino acid sequence selected from the group consisting of SEQ ID NOS: 21, 25, 29, and 30.

5. A nucleic acid encoding the polypeptide of claim 1.

6. An expression vector comprising the nucleic acid of claim 5 operatively linked to a control sequence.

7. A host cell comprising the expression vector of claim 6.

8. A pharmaceutical composition comprising:
(a) the polypeptide of claim 1; and
(b) a pharmaceutically acceptable carrier.

9. A pharmaceutical composition comprising:
(a) the polypeptide of claim 2; and
(b) a pharmaceutically acceptable carrier.

10. A pharmaceutical composition comprising:
(a) the polypeptide of claim 3; and
(b) a pharmaceutically acceptable carrier.

11. A pharmaceutical composition comprising:
(a) the polypeptide of claim 4; and
(b) a pharmaceutically acceptable carrier.

\* \* \* \* \*